(12) United States Patent
Tsimafeyeu

(10) Patent No.: US 10,358,499 B2
(45) Date of Patent: Jul. 23, 2019

(54) ANTIBODIES WHICH SPECIFICALLY BIND FIBROBLAST GROWTH FACTOR RECEPTOR 1, ENCODING NUCLEIC ACIDS THEREOF, AND METHODS OF PRODUCING THEREOF

(71) Applicant: LIMITED LIABILITY COMPANY "ONCOMAX" (LLC "ONCOMAX"), Moscow (RU)

(72) Inventor: Ilya Valerievich Tsimafeyeu, Moscow (RU)

(73) Assignee: LIMITED LIABILITY COMPANY "ONCOMAX" (LLC "ONCOMAX"), Moscow (RU)

( * ) Notice: Subject to any disclaimer, the term of this patent is extended or adjusted under 35 U.S.C. 154(b) by 0 days.

(21) Appl. No.: 15/763,750

(22) PCT Filed: Sep. 22, 2016

(86) PCT No.: PCT/RU2016/050041
§ 371 (c)(1),
(2) Date: Mar. 27, 2018

(87) PCT Pub. No.: WO2017/058062
PCT Pub. Date: Apr. 6, 2017

(65) Prior Publication Data
US 2018/0355045 A1    Dec. 13, 2018

(30) Foreign Application Priority Data

Sep. 28, 2015 (RU) ................................ 2015140935

(51) Int. Cl.
| | |
|---|---|
| *C12N 5/10* | (2006.01) |
| *A61K 39/00* | (2006.01) |
| *A61K 47/68* | (2017.01) |
| *A61P 35/00* | (2006.01) |
| *C07K 16/28* | (2006.01) |

(52) U.S. Cl.
CPC ...... *C07K 16/2863* (2013.01); *A61K 47/6803* (2017.08); *A61K 47/6849* (2017.08); *A61P 35/00* (2018.01); *C12N 5/10* (2013.01); *A61K 2039/505* (2013.01); *C07K 2317/21* (2013.01); *C07K 2317/24* (2013.01); *C07K 2317/73* (2013.01); *C07K 2317/76* (2013.01); *C07K 2317/92* (2013.01)

(58) Field of Classification Search
CPC ............ C07K 16/2863; C07K 2317/21; C07K 2317/24; C07K 2317/92; A61K 47/6803; A61K 47/6849; A61K 2039/505; A61P 35/00
See application file for complete search history.

(56) References Cited

U.S. PATENT DOCUMENTS

| | | |
|---|---|---|
| 4,399,216 A | 8/1983 | Axel et al. |
| 4,634,665 A | 1/1987 | Axel et al. |
| 4,816,567 A | 3/1989 | Cabilly et al. |
| 4,946,778 A | 8/1990 | Ladner et al. |
| 4,954,617 A | 9/1990 | Fanger et al. |
| 5,179,017 A | 1/1993 | Axel et al. |
| 5,225,539 A | 7/1993 | Winter |
| 5,530,101 A | 6/1996 | Queen et al. |
| 5,585,089 A | 12/1996 | Queen et al. |
| 5,693,762 A | 12/1997 | Queen et al. |
| 5,770,429 A | 6/1998 | Lonberg et al. |
| 5,939,598 A | 8/1999 | Kucherlapati et al. |
| 6,075,181 A | 6/2000 | Kucherlapati et al. |
| 6,114,598 A | 9/2000 | Kucherlapati et al. |
| 6,150,584 A | 11/2000 | Kucherlapati et al. |
| 6,162,963 A | 12/2000 | Kucherlapati et al. |
| 6,180,370 B1 | 1/2001 | Queen et al. |
| 2014/0086925 A1 | 3/2014 | Cool et al. |

FOREIGN PATENT DOCUMENTS

| | | |
|---|---|---|
| EP | 0 338 841 | 10/1989 |
| EP | 2 165 715 | 3/2010 |
| RU | 2287578 | 11/2006 |

(Continued)

OTHER PUBLICATIONS

Paul, WE. Fundamental Immunology, 3rd ed. Raven Press, NY, Chap. 9, pp. 292-295, 1993.*
Rudikoff S. et al. Proc. Natl. Acad. Sci. USA, 79:1979-1983, 1982.*
Colman, PM. Research in Immunology, Elsevier, NY, 145(1):33-36, 1994.*
International Search Resort issued in Appln. No. PCT/RU2016/050041 dated Mar. 6, 2017.

(Continued)

*Primary Examiner* — Robert S Landsman
(74) *Attorney, Agent, or Firm* — Nixon & Vanderhye P.C.

(57) ABSTRACT

The group of inventions relates to biotechnology and medicine and concerns antibodies for treating oncological diseases. The antibodies of the invention specifically bind and block fibroblast growth factor receptor 1 (FGFR1) and are characterized by amino acid sequences H-CDR1, H-CDR2, H-CDR3, L-CDR1, L-CDR2 and L-CDR3. A pharmaceutical composition for treating oncological diseases which contains antibodies of the invention, and a method for treating oncological diseases which involves administering a patient with antibodies of the invention are proposed. Also proposed are: a method for producing antibodies; nucleic acids which encode said antibodies; and cell lines for producing said antibodies. The use of the group of inventions makes it possible, with high effectiveness and specificity, to suppress the proliferation of tumor cells and inhibit tumor angiogenesis by means of blocking the FGF/FGFR1 pathological pathway, which in turn makes it possible to effectively treat oncological diseases.

17 Claims, No Drawings
Specification includes a Sequence Listing.

(56) References Cited

FOREIGN PATENT DOCUMENTS

| WO | WO 87/04462 | 7/1987 |
| WO | WO 88/00052 | 1/1988 |
| WO | WO 89/01036 | 2/1989 |
| WO | WO 01/09187 | 2/2001 |
| WO | WO 02/43478 | 6/2002 |
| WO | WO 2011/000384 | 1/2011 |

OTHER PUBLICATIONS

Timofeev I.V., "Retseptor faktora rosta fibroblastov 1-go tipa kak mishen tselenapravlennoi terapii pochechno-kletochnogo raka" *Sovremennaya Onkologiya*, vol. 15: 56-64 2013 , with Summary.

\* cited by examiner

ANTIBODIES WHICH SPECIFICALLY BIND FIBROBLAST GROWTH FACTOR RECEPTOR 1, ENCODING NUCLEIC ACIDS THEREOF, AND METHODS OF PRODUCING THEREOF

This application is the U.S. national phase of International Application No. PCT/RU2016/050041 filed Sep. 22, 2016 which designated the U.S. and claims priority to Russian Patent Application No. 2015140935 filed Sep. 28, 2015, the entire contents of each of which are hereby incorporated by reference.

SEQUENCE LISTING

The instant application contains a Sequence Listing which has been filed electronically in ASCII format.

The group of inventions relates to biotechnology and medicine, in particular, to new antibodies, which specifically bind fibroblast growth factor receptor 1, to production and use of antibodies for treatment of oncological diseases.

Excessive cell proliferation, as well as the formation of blood vessels in the tumor through which it feeds (angiogenesis), are known to account for malignant tumor growth.

The formation of new blood vessels results from the already existing endothelium and is a major component of many diseases and disorders, including tumor growth and metastasis, rheumatoid arthritis, psoriasis, atherosclerosis, diabetic retinopathy, retinopathy of prematurity, neovascular glaucoma, hemangiomas, immune rejection of corneal grafts and other grafted tissues, as well as chronic inflammation.

In the context of the tumor growth, angiogenesis is particularly important during the transition from hyperplasia to neoplasia, and to provide blood supply to a growing solid tumor (J. Folkman et al. Nature; 339, 58, 1989). Angiogenesis also allows tumors to be in contact with the host blood circulatory system, which allows determining directions to metastatic sites of tumor cells. Data supporting the role of angiogenesis in tumor metastasis were obtained, in particular, from studies proving that there is a relationship between the number and density of microvessels in invasive breast cancer and the actual presence of distant metastases (N. Weidner et al. New Eng. J. Med., 324:1, 1991).

According to numerous available data, both tumor cell, and endothelial cell proliferation can be caused by different naturally occurring polypeptides. The Fibroblast Growth Factor (FGF) family is one of them. The FGF was first discovered in pituitary extracts in 1973 (H. Armelin. PNAS 70, 9, 1973).

The FGF belongs to the family of heparin-binding polypeptides that modulate functions of different cells. The FGF has a strong effect on the proliferation and differentiation of tumor and endothelial cells. Currently, there are 23 members of the FGF family (FGF 1-23). Each family member has its own features. FGF 1 and 2 (acidic and base) are the most well characterized members. To affect the cells, the FGF must bind to the receptor on its surface. There are four types of FGF receptors (FGFR 1-4). FGFR1 binds not only to FGF 1 and to 2, but also with most other members of this family, so the role of the receptor in the transmittance of a signal into the cell is considered as the most significant one.

FGFR1 consists of an overmembrane, intramembrane and intracellular sections. The overmembrane section of the receptor consists of three domains (D similar to an immunoglobulin. FGFs usually interact with D II and III; heparan sulphate, participating in the formation of the FGF/FGFR1 complex, interacts with D III. The alternative mRNA splicing provides the formation of several FGFR1 variants on the cell surface (D Johnson, L. Williams. J Adv. Cancer Res., 60, 1, 1993; McKeehan et al. J Prog Nucleic Acid Res. Mol. Biol., 59, 135, 1998). The intracellular section of the receptor is represented by a tyrosine kinase, the autophosphorylation of which causes the further signal transduction into the cell nucleus, and cell division.

The applicant's authors have previously assumed and confirmed the emergence and achievement of a high level of FGFR1 expression both on primary renal cell carcinoma cells and in metastases of renal cell carcinoma (RCC) (I. Tsimafeyeu et al. ESMO-ECCO 09, 2009; WO2011000384). Moreover, it has been shown that the FGF/FGFR1 signaling pathway is not only independent during the development of RCC, but it can also determine resistance to existing targeted tumor therapy.

Other authors also showed that FGF/FGFR1 was of importance for the development of tumors such as non-small cell lung cancer, breast cancer, stomach and esophageal cancers, prostate cancer, bladder cancer, head and neck cancer, melanoma (C. Behrens et al. J Clinical cancer research 14, 19, 2008; M. Koziczak et al. J Oncogene, 23, 20 2004; K. Freier J Oral Oncology 43, 1, 2007; E. Shin et al. J Cancer Res Clin Oncol. 126, 9, 2000; K. Sugiura et al. J Oncology reports 17, 3, 2007; E. Devilard et al. J BMC Cancer 6, 272, 2006; G. Lefèvre et al. J Investigative Ophthalmology and Visual Science 50, 2009).

Based on the foregoing, it can be assumed that blocking the FGF/FGFR1 pathway may lead to the failure of the cancer cell proliferation, and to the inhibition of angiogenesis. FGFR1 antagonists, including human monoclonal antibodies, can be used to suppress tumor growth and its metastases.

SUMMARY OF THE INVENTIONS GROUP

The objective of the group of inventions is to create new antibodies to suppress the cancer cell proliferation, inhibit tumor angiogenesis, and treat oncological diseases. Another objective of the group of inventions is to scale up the number of aids for suppressing the cancer cell proliferation, inhibiting tumor angiogenesis and treating oncological diseases.

The subject of this invention is the antibody or its functional fragment, which specifically binds fibroblast growth factor receptor 1 that includes a heavy chain containing H-CDR1 with a SEQ ID NO:1 sequence or a SEQ ID NO:1 sequence version containing one or two conservative amino acid substitutions, H-CDR2 with a SEQ ID NO:2 sequence or a SEQ ID NO:2 sequence version containing one or two conservative amino acid substitutions, and H-CDR3 with a SEQ ID NO:3 or a SEQ ID NO:3 sequence version containing one or two conservative amino acid substitutions, and light chain containing L-CDR1 with a SEQ ID NO:4 sequence or a SEQ ID NO:4 sequence version containing one or two conservative amino acid substitutions, L-CDR2 with a SEQ ID NO:5 sequence or a SEQ ID NO:5 sequence version containing one or two conservative amino acid substitutions, and L-CDR3 with a SEQ ID NO:6 or a SEQ ID NO:6 sequence version containing one or two conservative amino acid substitutions.

In a particular embodiment, the antibody or its functional fragment is characterized by the said antibody or its functional fragment specifically binds to II and IIIc domains of the fibroblast growth factor receptor 1.

In a particular embodiment, the antibody or its functional fragment binds the fibroblast growth factor receptor 1 with a dissociation constant $K_d$ of $2 \times 10^{-9}$ M or less.

In a particular embodiment, the antibody or its functional fragment binds the fibroblast growth factor receptor 1 with a dissociation constant $K_d$ of $1.59 \times 10^{-9}$ M.

In a particular embodiment, the antibody or its functional fragment is characterized by that its heavy chain contains a variable domain with a sequence homologous to at least 90% of SEQ ID NO:7.

In a particular embodiment, the antibody or its functional fragment is characterized by that its heavy chain contains a variable domain with the SEQ ID NO:7 sequence.

In a particular embodiment, the antibody or its functional fragment is characterized by that its light chain contains a variable domain with a sequence homologous to at least 90% of SEQ ID NO:8.

In a particular embodiment, the antibody or its functional fragment is characterized by that its light chain contains a variable domain with the SEQ ID NO:8 sequence.

In a particular embodiment, the antibody or its functional fragment is characterized by that its heavy chain has a sequence homologous to at least 90% of SEQ ID NO:9.

In a particular embodiment, the antibody or its functional fragment is characterized by that its heavy chain has the SEQ ID NO:9 sequence.

In a particular embodiment, the antibody or its functional fragment is characterized by that its light chain has a sequence homologous to at least 90% of SEQ ID NO:10.

In a particular embodiment, the antibody or its functional fragment is characterized by that its light chain has the SEQ ID NO:10 sequence.

In a particular embodiment, the antibody or its functional fragment is characterized by that the said antibody is monoclonal.

In a particular embodiment, the antibody or its functional fragment is characterized by that the said antibody is chimeric, humanized or human.

In a particular embodiment, the antibody or its functional fragment is characterized by that the said antibody refers to the IgA, IgD, IgE, IgG1, IgG2, IgG3, IgG4, or IgM antibody isotype.

In a particular embodiment, the antibody or its functional fragment is characterized by that the said antibody is an antibody-cytotoxic agent conjugate.

The subject of this invention also includes a pharmaceutical composition for treating oncological diseases, which contains the aforesaid antibody or its functional fragment in an effective quantity and a pharmaceutically acceptable carrier.

In a particular embodiment, the pharmaceutical composition is characterized by that the renal cell carcinoma is an oncological disease.

The subject of this invention also includes the usage of the aforesaid antibody or its functional fragment for treating oncological diseases.

In a particular embodiment, the usage of the antibody or its functional fragment is characterized by that the renal cell carcinoma is an oncological disease.

A subject of this invention also includes a method of treating oncological diseases, which involves administering a patient with an effective quantity of the aforesaid antibody or its functional fragment or the aforesaid pharmaceutical composition.

Another subject of this invention includes a nucleic acid encoding the aforesaid antibody or its functional fragment.

In a particular embodiment, the nucleic acid is characterized by that it has a sequence homologous to at least 90% of SEQ ID NO:11.

In a particular embodiment, the nucleic acid is characterized by that it has the SEQ ID NO:11 sequence.

In a particular embodiment, the nucleic acid is characterized by that it has a sequence homologous to at least 90% of SEQ ID NO:12.

In a particular embodiment, the nucleic acid is characterized by that it has the SEQ ID NO:12 sequence.

Another subject of this invention includes the Chinese hamster ovary cell line containing the aforesaid nucleic acid to produce the aforesaid antibody or its functional fragment.

In a particular case, the Chinese hamster ovary cell line was deposited in the Russian National Collection of Industrial Microorganisms under the registration number VKPM H-134.

A further subject of this invention includes a method for producing The antibody or its functional fragment of the invention that includes culturing a cell line of the invention in the growth medium, and isolation of an antibody or it functional fragment from the aid cells and/or the said medium.

The technical result of the group of inventions is makes it possible, with high effectiveness and specificity, to suppress the proliferation of cancer cells and inhibit tumor angiogenesis by means of blocking the FGF/FGFR1 pathological pathway, which in turn makes it possible to treat oncological diseases effectively.

In a particular embodiment of the invention, which is the creation of a humanized antibody, an additional technical result is achieved: the unexpectedly high affinity and specificity of the antibody with virtually no detrimental antigenic (immunogenic) effects.

DETAILED SPECIFICATION

This invention relates to antibodies, in particular (as an option) to humanized monoclonal antibodies that bind specifically and with high affinity to FGFR1. In some embodiments, the antibodies have specific structural features, such as CDRs containing specific amino acid sequences. This invention relates to isolated antibodies, to methods for producing such antibodies, to immunoconjugates that include the said antibodies, as well as to pharmaceutical compositions containing the said antibodies. This invention also relates to methods of using these antibodies, e.g., for treating of diseases associated with FGFR1 expression, such as oncological diseases.

Pursuant thereto, this invention also relates to methods of using anti-FGFR1 antibodies of the invention for the treatment of different oncological diseases, e.g., for the treatment of renal cell cancer, lung cancer, and breast cancer.

For a better understanding of this invention, some terms used herein are set forth below.

As used herein, the term "antibody" means complete antibodies and any antigen-binding (functional) fragments (i.e., antigen-binding segments) or single chains of antibodies. The term "antibody" means a glycoprotein containing at least two heavy (H) chains and two light (L) chains connected by disulfide bonds, or its antigen-binding segment. Each heavy chain consists of the variable region of the heavy chain (VH) and the constant region of the heavy chain. The constant region of the heavy chain consists of three CH1, CH2 and CH3 domains. Each light chain consists of the variable region of the light chain (VL) and the constant region of the light chain. The constant region of the light chain consists of one CL domain. The VH and VL regions can be further subdivided into hypervariable regions, referred to as complementarity-determining regions (H-CDR and L-CDR) separated by more conservative regions called framework regions (FRs). Each VH and VL region consists of three CDRs and four FRs located from the N-terminus to the C-terminus as follows: FR1, CDR1, FR2, CDR2, FR3, CDR3, and FR4.

The variable regions of the heavy and light chains contain a binding domain that interacts with the antigen. Constant regions of antibodies can mediate the binding of immunoglobulin to host tissues or factors, including different cells of the immune system (e.g., excitatory cell) and the first component (C1q) of the classical complement cascade.

The term "antibody functional fragment" as used herein means one or more antibody fragments that keep their ability to bind specifically to an antigen (e.g., domains II and IIIc of FGFR1). It has been established that the unprocessed antibody fragments can performed an antigen-binding function of the antibody. Examples of binding fragments included in the definition of an antigen-binding regions of the antibody include (i) a Fab fragment, a monovalent fragment consisting of VL, VH, CL, and CH1 domains; (ii) a $F(ab')_2$ fragment, a divalent fragment comprising two Fab fragments bound by a disulfide bridge in the hinge region; (iii) a Fd fragment consisting of VH and CH1 domains; (iv) a Fv fragment consisting of VL and VH domains of one arm of the antibody; (v) a dAb fragment (Ward et al., 1989, Nature 341: 544-546) consisting of VH or VL domain; and (vi) an isolated complementarity-determining region (CDR). In addition, although the two domains of the Fv fragment, VL and VH, are encoded by different genes, they can be combined by recombinant DNA techniques using a synthetic linker that allows one to obtain a single protein chain in which the VL and VH regions pair to form monovalent molecules (known as a single-chain Fv fragment (scFv); e.g., refer to Bird et al., 1988, Science 242: 423-426, and Huston et al., 1988, Proc. Natl. Acad. Sci. USA 85:5879-5883). Such single-chain antibodies are also included into the definition of the term of the antigen-binding section of the antibody (antibody fragment). The said antibody fragments are produced by standard methods known by those skilled in the art, and examined for their suitability in the same way as intact antibodies. In one embodiment, the antibody fragment is selected from the group consisting of Fab, Fd, Fd', single-chain Fv (scFv), $scFv_a$ and domain-specific antibody (dAb).

In addition, the antibody or its functional fragment (antigen-binding section) may be a part of a larger immunoadhesive molecule formed by covalently or non-covalently binding of an antibody or antibody section to one or more other proteins or peptides. The said other proteins or peptides may have functional groups that make it possible to purify antibodies or their antigen-binding sections or to bind them to each other or to other molecules. Thus, examples of such immunoadhesive molecules include the usage of the central region of streptavidin to produce molecules containing a tetrameric single-chain variable fragment (scFv) (Kipriyanov et al., 1995, Human Antibodies and Hybridomas 6: 93-101), and the usage of a cysteine residue, marker peptide and C-terminal polyhistidine tag to create divalent and biotinylated scFv molecules (Kipriyanov et al., 1994, Mol. Immunol. 31:1047-1058). Antibody segments, such as Fab and $F(ab')_2$ fragments, can be produced from complete antibodies by standard methods, such as cleavage of complete antibodies using papain or pepsin. In addition, antibodies, antibody segments and immunoadhesive molecules can be produced by standard recombinant DNA techniques.

The antibody domains are complementary, since they belong to a family of structures that form related pairs or groups, or are separated from such families and retain the said feature. For example, the VH domain and the VL domain antibody are complementary; the two VH domains are not complementary, and the two VL domains are not complementary. Complementary domains can be found in other members of the immunoglobulin superfamily, such as γ- and δ- (or gamma and delta) domains of the T-cell receptor.

The term "domain" refers to the folded structure of a protein that preserves its tertiary structure independently of the rest of the protein. Domains are usually responsible for certain features of proteins, and in many cases they can be added, removed or transferred to other proteins without losing the function of the rest of the protein and/or domain. One variable domain of the antibody is a folded polypeptide domain comprising sequences that are characteristic of the variable regions of the antibody. Therefore, the antibody includes complete variable domains and modified variable domains in which, e.g., one or more loops are replaced by sequences that are not characteristic of antibody variable domains or antibody variable domains that have been truncated or include elongations at the N- or C-terminus, as well as folded fragments of variable domains that preserve at least partially binding activity and specificity of the unprocessed domain.

The variable domains of this invention can be combined to form a domain group; e.g., complementary domains can be combined, in particular, VL domains can be combined with VH domains. Noncomplementary domains can also be combined. Domains can be combined in many ways, including domain binding by covalent or noncovalent interactions.

The term "recombinant antibody" means produced, expressed, created or isolated antibodies by recombinant methods, e.g., antibodies expressed by a recombinant expression vector transfected into a host cell; antibodies isolated from the combinatorial library of recombinant antibodies; antibodies isolated from an animal (e.g., a mouse) that is transgenic for human immunoglobulin genes (refer to, for example, Taylor et al., 1992, Nucl. Acids Res. 20: 6287-6295), or antibodies obtained, expressed, created or isolated by any other method, which involves splicing of specific sequences of immunoglobulin genes (such as sequences of human immunoglobulin genes) into other DNA sequences. Examples of recombinant antibodies include chimeric, CDR-implanted and humanized antibodies.

The term "human antibody" means antibodies with variable and constant regions corresponding to or isolated from human germline immunoglobulin sequences described, e.g., by Kabat et al. (refer to Kabat et al., 1991, Sequences of Proteins of Immunological Interest, Fifth Edition, US Department of Health and Human Services, NIH Publication 91-3242). However, the human antibodies of this invention may include amino acid residues not encoded by human germline immunoglobulin sequences (e.g., mutations introduced by nonspecific or site-specific in vitro mutagenesis or in vivo somatic mutation), e.g., in the CDR and, in particular, in CDR3.

The recombinant human antibodies of this invention contain variable regions and may also include constant regions derived from human germline immunoglobulin sequences (refer to the article by Kabat et al., (1991)

Sequences of Proteins of Immunological Interest, Fifth Edition, U.S. Department of Health and Human Services, NIH Publication 91-3242). However, in some embodiments, such recombinant human antibodies are subjected to in vitro mutagenesis (or in vivo somatic mutagenesis using an animal that is transgenic to human Ig sequences), and thus, the amino acid sequences of the VH and VL regions of recombinant antibodies are sequences that, being isolated and related sequences of the VH and VL regions of the human germ line, may not exist under natural conditions in the spectrum of in vivo germline antibody sequences. However, in some embodiments, such recombinant antibodies are the result of selective mutagenesis, reverse mutation, or both.

The term "reverse mutation" means a process in which some or all of the somatically mutated amino acids of a human antibody are replaced with corresponding residues from a homologous germline antibody sequence. The heavy and light chain sequences of the human antibody of this invention are separately subjected to a comparative analysis with germline sequences in the VBASE database to identify sequences with the highest homology. The differing amino acids of the human antibody of this invention are returned to the germline sequence by mutating nucleotides at specific positions encoding a different amino acid. The role of each amino acid identified in such a manner, as a candidate for reverse mutation should be investigated for direct or indirect antigen binding, herewith, any amino acid that is found to effect any desired characteristics of the human antibody after the mutation should not be included into the final human antibody. To minimize the number of amino acids subjected to a reverse mutation, the amino acids at positions that are found to differ from the nearest germline sequence, but are identical to the corresponding amino acid in the second germline sequence, may remain, provided that the second germline sequence is identical and corresponds to the sequence of the human antibody of this invention with respect to at least 10, preferably 12 amino acids, on both terminals of the considered amino acid. Reverse mutation can occur at any stage of antibody optimization.

The term "chimeric antibody" means an antibody comprising sequences of the variable region of heavy and light chain of one origin, and a constant region sequence of another origin, e.g., antibodies comprising the heavy and light chain variable regions of the rodent associated with human constant regions.

The term "humanized antibody" means antibodies comprising sequences of the variable region of heavy and light chain of an origin other than human (e.g., mouse), but in which at least a section of the VH and/or VL region sequence has been altered to be more similar to human, that is more similar to the variable sequences of the human germline. One type of a humanized antibody is a CDR-implanted antibody in which human CDR sequences are inserted into VH and VL regions other than human sequences with an aim to replace corresponding CDR sequences other than human. Methods for humanizing antibodies other than human are well known in the art. The humanized antibody typically contains one or more amino acid residues inserted therein from a source other than the human one. The said amino acid residues, other than human, are often identified as foreign residues that are typically derived from a foreign variable domain. Humanization can be performed by a method developed by Winter and co-authors (Jones et al., Nature, 321: 522-525, 1986; Riechmann et al., Nature, 332: 323-327, 1988; Verhoeyen et al., Science, 239: 1534-1536, 1988), which involves replacing the corresponding sequences of the human antibody with CDR regions or CDR sequences other than human (e.g., rodent). Thus, such humanized antibodies are chimeric antibodies (U.S. Pat. No. 4,816,567) in which substantially a section of the intact human variable domain is replaced by a corresponding sequence of an origin other than human. In practice, humanized antibodies are generally represented by human antibodies in which some CDR residues and, possibly, some framework region (FRs) residues are replaced by residues from similar sites in rodent antibodies. Supplementary materials that describe the humanization process include the articles by Sims et al., J. Immunol., 151:2296, 1993; Chothia et al., J. Mol. Biol., 196:901, 1987; Carter et al., Proc. Natl. Acad. Sci. USA, 89:4285, 1992; Presta et al., J. Immunol., 151: 2623, 1993, which are included in this specification of the invention as a reference.

The term "polyclonal antibodies" means antibodies that are typically a mixture of antibodies specific for a particular antigen but binding to different epitopes on the said antigen. Polyclonal antibodies are usually formed in the animal body as a result of several subcutaneous (sc) or intraperitoneal (ip) injections of the related antigen and adjuvant. It may be useful to conjugate the related antigen to a protein that is immunogenic in an immunized form, such as, e.g., cochlear lymph glomocyanin, serum albumin, bovine thyroglobulin or soybean trypsin inhibitor, using a bifunctional or derivatizing agent, e.g., maleimidobenzoyl sulfosuccinimide ester (conjugation for cysteine residues), N-hydroxysuccinimide (for lysine residues), glutaraldehyde, succindialdehyde, $SOCl_2$ or $R_1NCNR$, where R and $R_1$ are different alkyl groups. Methods for producing polyclonal antibodies are known in the art and are described, e.g., in the article Antibodies: A Laboratory Manual, Lane and Harlow, 1988, which is included in this specification of the invention as a reference.

The term "monoclonal antibodies" as used herein means an antibody derived from a hybridoma (e.g., an antibody secreted by a hybridoma obtained by hybrid assay, such as the standard hybridoma technique by Kohler and Milstein). For example, monoclonal antibodies can be produced by a hybrid method first described in the article by Kohler et al., Nature, 256:495, 1975, or can be produced by recombinant DNA techniques (U.S. Pat. No. 4,816,567). Monoclonal antibodies are produced from a population of substantially homogeneous antibodies, i.e., individual antibodies that form a population are identical except for possible natural mutations that may be present in small amounts. Thus, the term "monoclonal" determines the nature of the antibody, which is not a mixture of individual antibodies.

As used herein, the terms "antigen-recognizing antibody" and "antigen-specific antibody" and "antigen antibody" are synonymous with the term "antibody that specifically binds to the antigen".

The term "derived antibodies" means any modified form of an antibody (human, humanized, murine), e.g., an antibody conjugate with another agent or antibody.

The term "antibody that specifically binds the fibroblast growth factor receptor 1 (FGFR1)" as used herein means an antibody that binds to human FGFR1 with $K_d=1\times10^{-7}$ M or less, more preferably $1\times10^{-8}$ M or less, even more preferably $2\times10^{-9}$ M or less, and most preferably $1.59\times10^{-9}$ M or less.

The term "high affinity" to an IgG antibody as used herein means that the antibody binds to a target antigen with $K_d$ of $1\times10^{-7}$ M or less, more preferably $1\times10^{-8}$ M or less, still more preferably $2\times10^{-9}$ M or less, and most preferably $1.59\times10^{-9}$ M or less.

Each of the above amino acid and nucleotide sequences is shown in the following Table 1 and in the List of Sequences.

TABLE 1

Sequences of variable and constant regions and corresponding heavy and light chain CDRs of anti-FGFR1 antibodies

| Number | Type | Description | Sequence |
|---|---|---|---|
| SEQ ID NO: 1 | amino acid | H-CDR1 | GYSITSDYA |
| SEQ ID NO: 2 | | H-CDR2 | ITYSGTT |
| SEQ ID NO: 3 | | H-CDR3 | ARDGNYFDY |
| SEQ ID NO: 4 | | L-CDR1 | SSVSSSY |
| SEQ ID NO: 5 | | L-CDR2 | RTS |
| SEQ ID NO: 6 | | L-CDR3 | QQWSGYPLT |
| SEQ ID NO: 7 | | VH | QVQLQESGPGLVKPSQTLSLTCTVSGYSITSDYAWSIRQHPGKGLEWIG YITYSGTTYYNPSLKSRVTISVDTSKNQFSLKLSSVTAADTAVYYCARDGNY FDYWGQGTLVTVSS |
| SEQ ID NO: 8 | | VL | DIQLTQSPSFLSASVGDRVTITCRASSSVSSSYLHWYQQKPGKAPKLLIYRT STLQSGVPSRFSGSGSGTEFTLTISSLQPEDFATYYCQQWSGYPLTFGGG TKVEIK |
| SEQ ID NO: 9 | | heavy chain | QVQLQESGPGLVKPSQTLSLTCTVSGYSITSDYAWSIRQHPGKGLEWIG YITYSGTTYYNPSLKSRVTISVDTSKNQFSLKLSSVTAADTAVYYCARDGNY FDYWGQGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNH KPSNTKVDKRVEPKSCDKTHTCPPCPAPELLGGPSVFLFPPKPKDTLMISR TPEVICVVVDVSHEDPEVKFNWYVDGVEVHNAKTKPREEQYNSTYRVVS VLTVLHQDWLNGKEYKCKVSNKALPAPIEKTISKAKGQPREPQVYTLPPSR EEMTKNQVSLTCLVKGFYPSDIAVEWESNGQPENNYKTTPPVLDSDGSFF LYSKLTVDKSRWQQGNVFSCSVMHEALHNHYTQKSLSLSPGK |
| SEQ ID NO: 10 | | light chain | DIQLTQSPSFLSASVGDRVTITCRASSSVSSSYLHWYQQKPGKAPKLLIYRT STLQSGVPSRFSGSGSGTEFTLTISSLQPEDFATYYCQQWSGYPLTFGGG TKVEIKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLS SPVTKSFNRGEC |
| SEQ ID NO: 11 | nucleotide | encodes the heavy chain | AAGCTTGCCGCCACCATGAGAGTGCTGATTCTTTTGTGGCTGTTCACAG CCTTTCCTGGTATCCTGTCTCAGGTGCAGCTGCAGGAGTCGGGCCCAG GACTGGTGAAGCCTTCACAGACCCTGTCCCTCACCTGCACTGTCTCTG GCTACTCAATCACCAGTGATTATGCCTGGAGCTGGATCCGCCAGCACC CAGGGAAGGGCCTGGAGTGGATTGGGTACATAACCTACAGTGGTACCA CTTACTACAACCCGTCCCTCAAGAGTCGAGTTACCATATCAGTAGACAC GTCTAAGAACCAGTTCTCCCTGAAGCTGAGCTCTGTGACTGCCGCGGA CACGGCCGTGTATTACTGTGCAAGAGATGGTAACTACTTTGACTACTGG GGCCAAGGAACCCTGGTCACCGTCTCCTCAGCGTCGACCAAGGGCCC ATCGGTCTTCCCCCTGGCACCCTCCTCCAAGAGCACCTCTGGGGGCAC AGCGGCCCTGGGCTGCCTGGTCAAGGACTACTTCCCCGAACCGGTGA CGGTGTCGTGGAACTCAGGCGCCCTGACCAGCGGCGTGCACACCTTC CCGGCTGTCCTACAGTCCTCAGGACTCTACTCCCTCAGCAGCGTGGTG ACCGTGCCCTCCAGCAGCTTGGGCACCCAGACCTACATCTGCAACGTG AATCACAAGCCCAGCAACACCAAGGTGGACAAGAGAGTTGAGCCCAAA TCTTGTGACAAAACTCACACATGCCCACCGTGCCCAGCACCTGAACTCC TGGGGGGACCGTCAGTCTTCCTCTTCCCCCCAAAACCCAAGGACACCC TCATGATCTCCCGGACCCCTGAGGTCACATGCGTGGTGGTGGACGTGA GCCACGAAGACCCTGAGGTCAAGTTCAACTGGTACGTGGACGGCGTG GAGGTGCATAATGCCAAGACAAAGCCGCGGGAGGAGCAGTACAACAG CACGTACCGTGTGGTCAGCGTCCTCACCGTCCTGCACCAGGACTGGCT GAATGGCAAGGAGTACAAGTGCAAGGTCTCCAACAAAGCCCTCCCAGC CCCCATCGAGAAAACCATCTCCAAAGCCAAAGGGCAGCCCCGAGAACC ACAGGTGTACACCCTGCCCCCATCCCGGGAGGAGATGACCAAGAACCA GGTCAGCCTGACCTGCCTGGTCAAAGGCTTCTATCCCAGCGACATCGC CGTGGAGTGGGAGAGCAATGGGCAGCCGGAGAACAACTACAAGACCA CGCCTCCCGTGCTGGACTCCGACGGCTCCTTCTTCCTCTATAGCAAGC TCACCGTGGACAAGAGCAGGTGGCAGCAGGGGAACGTCTTCTCATGCT CCGTGATGCATGAGGCTCTGCACAACCACTACACGCAGAAGAGCCTCT CCCTGTCCCCGGGTAAATAATCTAGA |
| SEQ ID NO: 12 | | encodes the light chain | AAGCTTGCCGCCACCATGGATTTACAGGTGCAGATTATCAGCTTCCTGC TAATCAGTGTCACAGTCATAATGTCCAGAGGAGACATCCAGTTGACCCA GTCTCCATCCTTCCTGTCTGCATCTGTAGGAGACAGAGTCACCATCACT TGCCGGGCCAGTTCAAGTGTAAGTTCCAGTTACTTACACTGGTATCAGC AAAAACCAGGGAAAGCCCCTAAGCTCCTGATCTATAGGACATCCACTTT GCAAAGTGGGGTCCCATCAAGGTTCAGCGGCAGTGGATCTGGGACAG AATTCACTCTCACAATCAGCAGCCTGCAGCCTGAAGATTTTGCAACTTA TTACTGTCAGCAGTGGAGTGGTTACCCATTGACGTTCGGCGGAGGGAC CAAGGTGGAGATCAAACGAACTGTGGCTGCACCAAGTGTCTTCATCTTC CCGCCATCTGATGAGCAGTTGAAATCTGGAACTGCCTCTGTTGTGTGCC TGCTGAATAACTTCTATCCCAGAGAGGCCAAAGTACAGTGGAAGGTGG ATAACGCCCTCCAATCGGGTAACTCCCAGGAGAGTGTCACAGAGCAGG ACAGCAAGGACAGCACCTACAGCCTCAGCAGCACCCTGACGCTGAGCA AAGCAGACTACGAGAAACACAAAGTCTACGCCTGCGAAGTCACCCATC AGGGCCTGAGCTCGCCCGTCACAAAGAGCTTCAACAGGGGAGAGTGTT AATCTAGA |

Homologous Antibodies

In some embodiments, the antibody of the invention comprises heavy and light chain variable regions comprising amino acid sequences homologous to the amino acid sequences of the preferred antibodies described herein, wherein the said antibodies retain the desired functional properties of the anti-FGFR1 antibodies of the invention.

Homologous antibodies can be obtained by mutagenesis (e.g., site-directed or PCR-mediated mutagenesis) of the corresponding nucleic acid molecules, followed by testing the encoded modified antibody to preserve its functions according to the functional assays described herein.

The term "homology percent of two amino acid sequences" as used herein is equivalent to the term "percent identity of two sequences". The percent identity of two sequences depends on the number of positions of identical amino acids in these two sequences (i.e., % of homology=% of identical amino acids at these positions/total number of positions×100), taking into account the number of gaps and the length of each gap to be entered for optimal comparison of the two sequences by alignment.

The percent identity of the two amino acid sequences can be determined using an algorithm by E. Meyers and W. Miller (Comput. Appl. Biosci., 4:11-17, 1988), which was entered into the ALIGN program (version 2.0), using the table of "balances" of PAM120 residues, a penalty for a gap-lengthening=12, and a penalty for a gap-space=4. In addition, the percent identity of the two amino acid sequences can be determined using the Needleman and Wunsch algorithm (J. Mol. Biol. 48: 444-453, 1970), which was entered into the GAP program included in the GCG software package (available at www.gcg.com), using either the Blossum 62 matrix or the PAM250 matrix and the "weights" of gaps-spaces comprising 16, 14, 12, 10, 8, 6, or 4, and "balances" of lengths (sections) comprising 1, 2, 3, 4, 5 or 6.

The protein sequences of the invention can additionally or alternatively be used as a "requested sequence" to perform a search in public databases, e.g., to identify related sequences. This can be done using the Xblast software (version 2.0) Altschul, et al., 1990, J. Mol. Biol. 215:403-10. The search for BLAST proteins can be performed using the XBLAST program, where with a "balancing factor" of 50 and a word length of three, amino acid sequences homologous to the antibody molecule sequences of the invention can be obtained. To perform alignment with spaces for sequence matching, the Gapped BLAST program described by Altschul et al., 1997, Nucleic Acids Res. 25 (17): 3389-3402 can be used. When working with BLAST and Gapped BLAST programs, the default parameters set in the corresponding programs (e.g., XBLAST and NBLAST) can be used. Refer to www.ncbi.nlm.nih.qov.

Nucleic Acid Molecules Encoding Antibodies According to this Invention

In another aspect, this invention relates to nucleic acid molecules encoding antibodies of the invention. Such nucleic acids may be present in whole cells, in cell lysates or in partially purified or in substantially pure form. The nucleic acid is an "isolated" or "substantially pure" one if it is purified from other cellular components or other impurities, e.g., from other cellular nucleic acids or proteins, using standard methods, including alkali/SDS treatment, centrifugation in a CsCl density gradient, a column chromatography, agarose gel electrophoresis, and other methods well known to those skilled in the art. Refer to F. Ausubel, et al., ed., 1987, Current Protocols in Molecular Biology, Greene Publishing and Wiley Interscience, New York. The nucleic acid of the invention may be, for example, DNA or RNA, and may or may not contain intronic sequences. In a preferred embodiment of the invention, the nucleic acid is a cDNA molecule.

Nucleic acids of the invention may be produced by standard molecular biology techniques. For antibodies expressed by hybridomas (e.g., hybridomas derived from transgenic mice carrying the human immunoglobulin genes), cDNAs encoding the light and heavy chains of the antibody produced by the hybridomas can be produced by standard PCR amplification or cDNA cloning techniques. For antibodies derived from the library of immunoglobulin genes (e.g., using representation methods of phage sequences), the nucleic acid encoding the antibody can be isolated from this library.

Preferred nucleic acid molecules of the invention are molecules encoding the VH and VL sequences of a monoclonal anti-FGFR1 antibody. The DNA sequence encoding the VH sequence of the anti-FGFR1 antibody is SEQ ID NO:11. The DNA sequence encoding the VL sequence of the anti-FGFR1 antibody is SEQ ID NO:12. After obtaining DNA fragments encoding VH and VL segments, these DNA fragments can then be modified by standard recombinant DNA techniques, e.g., for the conversion of variable region genes into genes encoding the full-length antibody chain into the Fab fragment or the scFv gene. In these manipulations, the VL or VH-encoding DNA fragment is operably linked to another DNA fragment encoding another protein, such as an antibody constant region or a flexible linker. The term "functionally linked" as used herein means that two DNA fragments are linked to each other in such a manner that the amino acid sequences are encoded by these two DNA fragments while preserving the reading frame. The isolated DNA encoding the VH region can be transformed into a gene encoding the full-length heavy chain by the functional addition of the VH-encoding DNA to another DNA molecule encoding the constant regions of the heavy chain (CH1, CH2 and CH3). The sequences of the constant region genes of the human heavy chain are known to those skilled in the art (refer to, e.g., Kabat, E. A., el al., 1991, Sequences of Proteins of Immunological Interest, Fifth Edition, U.S. Department of Health and Human Services, NIH Publication 91-3242), and DNA fragments including these regions can be obtained by a standard PCR amplification method. The constant region of the heavy chain can include the IgG1, IgG2, IgG3, IgG4, IgA, IgE, IgM or IgD constant regions, and, most preferably, the IgG1 constant region. For the heavy chain Fab fragment, the VH-encoding DNA can be operably linked to another DNA molecule encoding only the heavy chain constant region CH1. The isolated DNA encoding the VL region can be transferred into the full-length light chain gene (as well as the Fab light chain gene) by the functional addition of the VL-encoding DNA to another DNA molecule encoding the light chain constant region, CL. The constant region of the light chain can include the kappa or lambda constant region, and, most preferably, the kappa constant region. To create the scFv gene, the VH- and VL-encoding DNA fragments are functionally linked to another fragment encoding a flexible linker, e.g., encoding the amino acid sequence $(Gly_4\text{-}Ser)_3$, so that the VH and VL sequences can be expressed as a whole single-chain protein, wherein the said VL and VH regions are linked to each other via a flexible linker (refer to, e.g., Bird et al., 1988, Science 242: 423-426; Huston et al., 1988, Proc. Natl. Acad. Sci. USA 85:5879-5883; McCafferty et al., 1990, Nature 348:552-554).

Production of Monoclonal Antibodies According to this Invention

Monoclonal antibodies (mAbs) of the invention can be produced by various methods, including standard technique for the monoclonal antibody production, e.g., the standard method for hybridizing somatic cells, described by Kohler and Milstein, 1975, Nature 256: 495. Other methods of monoclonal antibody production can also be used, e.g., viral or oncogenic transformation. A preferred animal that can be used to produce a hybridoma is a rodent, e.g., mouse. The production of a hybridoma in a mouse is a well-developed procedure. Immunization protocols and methods for isolating immunized splenocytes for fusion morphogenesis are known to those skilled in the art. Cell fusion partners (e.g., murine myeloma cells) and procedures for such fusion are also known to those skilled in the art. In the production of monoclonal antibodies by a hybridoma method, a mouse or other suitable host animal is immunized with an antigen by subcutaneous, intraperitoneal or intramuscular injection to identify lymphocytes that produce or are capable of producing antibodies that specifically bind to the protein(s) used for immunization. As an alternative, lymphocytes can be immunized in vitro. The lymphocytes are then fused with myeloma cells using an appropriate agent, for example, such as polyethylene glycol, to create a hybridoma cell (J. Coding. Monoclonal Antibodies: Principles and Practice, pp. 59-103, Academic Press, 1986).

In this invention, such antigen is represented by FGFR1 (II and IIIc domains). The antigen may be represented by a fragment or part of FGFR1 having one or more amino acid residues that are involved in the FGF binding.

The hybridoma cells prepared in this manner are plated out and cultivated in a suitable culture medium, which should preferably contain one or more substances that inhibit the growth or survival of non-fused, parental myeloma cells. For example, if there is no enzyme hypoxanthine-guanine phosphoribosyltransferase (HGPRT or HPRT) in parental myeloma cells, the hybridoma culture medium will usually contain hypoxanthine, aminopterin and thymidine (HAT medium), which inhibit the growth of cells having no HGPRT. It is preferable to select such myeloma cells that fuse efficiently, maintain a stable high level of antibody expression in the selected antibody producing cells, and are sensitive to media such as, e.g., HAT medium. Preferred cell lines among such cells include: murine myeloma lines, such as lines derived from murine MOPC-21 and MPC-11 tumors, which can be obtained from the Cell Distribution Center of the Salk Institute for Biological Studies in San Diego (California, USA); SP-2 cells, which can be obtained from the American Type Culture Collection in Rockville (Maryland, USA); and the P3X63Ag8U.1 cells described by Yelton et al. (J Curr. Top. Microbiol. Immunol. 81, 1, 1978). In addition, cell lines of human myeloma and human-mouse heteromyeloma capable of producing human monoclonal antibodies have been described (D. Kozbor et al. J Immunol. 133, 3001, 1984; B. Brodeur, P. Tsang Monoclonal Antibody Production Techniques and Applications, pp. 51-63, Marcel Dekker Inc., New York, 1987). The culture medium in which hybridoma cells are grown is subject to analysis for the production of monoclonal antibodies directed against the corresponding antigen. The binding specificity of monoclonal antibodies produced by hybridoma cells is preferred to be high.

This invention includes those monoclonal antibodies that showed high specificity ($2\times10^{-9}$ or less) of binding to these antigens, determined by the standard BIOCORE technique.

The chimeric or humanized antibodies of the invention can be derived from the murine monoclonal antibody sequence prepared as described above. The DNA encoding the heavy and light chains of the immunoglobulin can be isolated from a nonhuman hybridoma of interest and constructed by standard molecular biology techniques so that it contains humanized immunoglobulin sequences. Thus, for example, to create a chimeric antibody, murine variable regions can be linked to human constant regions by methods known to those skilled in the art (refer to, e.g., U.S. Pat. No. 4,816,567, Cabilly et al.). To create a humanized antibody, murine CDRs can be incorporated into the human framework region by methods known to those skilled in the art (refer to, e.g., U.S. Pat. No. 5,225,539, Winter and U.S. Pat. Nos. 5,530,101; 5,585,089; 5,693,762; and 6,180,370, Queen et al.). In a preferred embodiment, humanized monoclonal antibodies are the antibodies of the invention. In another embodiment, the human antibodies of the invention can be produced in mice having human immunoglobulin sequences in transgens and in transchromosomes, for example in mice that have a human heavy chain transgene and a human light chain transchromosome. Such mice, referred to herein as the "KM" mice, are described in detail in International Application WO2002043478, Ishida et al. In addition, alternative transgenic animal systems expressing human immunoglobulin genes are known to those skilled in the art and can be used to produce anti-FGFR1 antibodies of the invention. For example, an alternative transgenic system, called Xenomouse (Abgenix, Inc.) can be used; and such mice are described, for example, in U.S. Pat. Nos. 5,939,598; 6,075,181; 6,114,598; 6,150,584 and U.S. Pat. No. 6,162,963 patents, Kucherlapati et al. Moreover, alternative transchromosomal animal systems expressing human immunoglobulin genes are known to those skilled in the art and can be used to produce anti-FGFR1 antibodies of the invention. Thus, for example, mice carrying a heavy chain transchromosome and a light chain transchromosome can be used and called "TC mice"; and such mice are described in an article by Tomizuka et al., 2000, Proc. Natl. Acad. Sci. USA 97:722-727. In addition, cows carrying human heavy and light chain transchromosomes as described in the literature (Kuroiwa et al., 2002, Nature Biotechnology 20: 889-894) can be used to produce the anti-FGFR1 antibody of the invention. The monoclonal antibodies of the invention can also be produced using phage representation techniques for screening immunoglobulin gene libraries. Such phage presentation techniques for isolating antibodies are known to those skilled in the art. Refer to, for example, U.S. Pat. Nos. 5,223,409; 5,403,484 and 5,5711,698, Ladner et al.; U.S. Pat. Nos. 5,427,908 and 5,580,717, Dower et al.; U.S. Pat. Nos. 5,969,108 and 6,172,197, McCafferty et al.; and U.S. Pat. Nos. 5,885,793; 6,521,404; 6,544,731; 6,555,313; 6,582,915 and 6,593,081, Griffiths et al.

The monoclonal antibodies of the invention can also be produced using SCID mice that have been injected with human immune cells reconstructed so that these mice could produce a human antibody after the immunization. Such mice are described, for example, in U.S. Pat. Nos. 5,476,996 and 5,698,767 patents, Wilson et al.

Immunization of Mice Producing Anti-FGFR1 Antibody

If Ig producing mice are used to produce antibodies of the invention, such mice can be immunized with an FGFR1-expressing cell line, purified FGFR1 antigen or a preparation enriched with this antigen. The preferred age of mice should be 6-16 weeks after the immunization. For example, a purified or recombinant preparation (5-50 μg) of the FGFR1 antigen can be used for intraperitoneal immunization of mice producing an anti-FGFR1 antibody. A detailed description of the procedures for the preparation of anti-FGFR1 antibodies is given in Example 1 below. Cumulative results of study on various antigens have shown that an immune response was observed in transgenic mice, when their primary intraperitoneal immunization (i.p.) was performed with antigen in complete Freund's adjuvant, and then the i.p. immunization with an antigen in incomplete Freund's adjuvant was every performed two weeks (6 total immunizations).

However, it has also been found that, in addition to Freund's adjuvant, other adjuvants are effective. In addition, it was found that, in the absence of an adjuvant, the whole cells are highly immunogenic. Monitoring of the immune response can be performed during the entire immunization procedure with plasma samples obtained from the retroorbital region. This plasma can be screened by ELISA, and mice that have sufficiently high titers of anti-FGFR1 antibodies can then be used to fuse the cells. Mice can be intravenously reinjected with antigen 3 days before their sacrifice and sampling their spleen. It is assumed that 2-3 cell fusion procedures may be required for each immunization. Typically, 6-24 mice are immunized with each antigen. HCo7 and HCo12 strains are commonly used for this purpose. Generation of murine HCo7 and HCo12 strains is described in U.S. Pat. No. 5,770,429 patent and in Example 2 of WO2001009187 application, respectively.

In addition, both HCo7 and HCo12 transgenes can be transferred together to one mouse having two different human heavy chain transgenes (HCo7/HCo12). The KM strain mice described in WO2002043478 can be alternatively or additionally used.

Generation of Hybridomas Producing Anti-FGFR1 Antibodies Under this Invention

To generate hybridomas producing anti-FGFR1 antibodies of the invention, splenocytes and/or lymph node cells taken from immunized mice can be isolated and fused to an appropriate immortalized cell line, such as a murine myeloma cell line. The hybridomas produced can be screened for the production of antigen-specific antibodies. For example, single-cell suspensions of spleen lymphocytes taken from immunized mice can be fused to ⅓ of the number of non-secretory cells of murine myeloma Sp2/0 (ATCC, CRL 1581) linked to 50% PEG. As an alternative, single-cell suspensions of spleen lymphocytes from immunized mice can be fused with an equal number of murine Sp2/0 myeloma cells using an electric field electrospraying method using the Cyto Pulse large chamber cell fusion electroporator (Cyto Pulse Sciences, Inc., Glen Burnie, Md.). Cells are plated at a concentration of about $1 \times 10^5$ cells/well in a flat-bottomed microtiter plate and then incubated in a selective medium containing 10% fetal bovine serum (Hyclone, Logan, Utah), 10% P388DI conditioned medium (ATCC, CRL TIB-63), 3-5% Origen (IGEN) in DMEM (Mediatech, CRL 10013, high glucose, L-glutamine and sodium pyruvate), as well as 5 mM HEPES, for two weeks; cells can be cultured in a medium where HAT (hypoxanthine-aminopterin-thymidine) medium was replaced by HT medium. Individual wells can then be screened by ELISA or FACS for monoclonal IgG antibodies. Positive clones can then be screened for FGFR1-positive antibodies by ELISA or against FGFR1-expressing cells. After intensive growth of the hybridomas, the medium is monitored usually in 10-14 days. Antibody-secreting hybridomas can be re-plated and re-screened, and upon obtaining a positive result on the anti-FGFR1 antibody, the antibodies can be subcloned by limiting dilution at least twice. Then, stable subclones can be cultured in vitro to generate small amounts of antibodies in a tissue culture medium for characterization purposes.

To purify anti-FGFR1 antibodies, the selected hybridomas can be cultured in two-liter centrifuge flasks designed to purify monoclonal antibodies.

Supernatants can be filtered and concentrated, and then subjected to protein affinity chromatography on A-Sepharose (Pharmacia, Piscataway, N.J.). To ensure the desired purity, eluted IgG can be assessed by gel electrophoresis and high performance liquid chromatography. The buffer solution can be replaced with PBS, and the concentration can be determined by $OD_{280}$ using an extinction coefficient of 1.43. Monoclonal antibodies can be divided into aliquots and stored at −80° C.

Generation of Transfectomas Producing Monoclonal Antibodies Under this Invention Antibodies of the invention can also be produced in a transfectoma of host cells using combined recombinant DNA techniques and gene transfection. For example, for the expression of antibodies or its fragments, DNA encoding partial or full length light and heavy chains can be obtained by standard molecular biology techniques (for example, by PCR amplification or cDNA cloning using a hybridoma expressing the antibody of interest—a detailed description of the procedures for the production of a recombinant DNA encoding the light or heavy chain of the antibody of the invention is given in Example 5), and these DNAs can be inserted into the expression vectors so that such genes are functionally linked to the sequences of transcription and translation regulation. In this context, the term "functionally linked" means that the antibody gene is ligated into a vector in such a manner that the said transcriptional and translational regulation sequences in the vector perform their inherent function of regulating the transcription and translation of the antibody gene. The expression vector and expression control sequences are selected so that they are compatible with the host cell used for such expression. The antibody light chain gene and antibody heavy chain gene may be inserted into separate vectors, or, more often, both genes are inserted into the same expression vector. The antibody genes are inserted into the expression vector by standard methods (for example, by ligation on complementary restriction sites into antibody gene fragments and into a vector, or by blunt-end ligation if such restriction sites are not available—a detailed description of the procedures for the production of a plasmid containing recombinant DNA encoding the light and the heavy chain of the antibody of the invention is given in Example 5). The variable regions of the light and heavy chains of antibodies described herein can be used to create full-length genes encoding an antibody of any isotype by inserting them into expression vectors already encoding the heavy and light chain constant regions of the antibody of the required isotype so that the VH segment is functionally linked to the CH segment(s) in the vector, and the VL segment was functionally linked to the CL segment in the given vector. In addition or as an alternative, the recombinant expression vector may encode a signal peptide that facilitates the secretion of the antibody chain from the host cell. The specified antibody chain gene can be cloned into a vector in such a manner that the signal peptide is linked to the N-terminus of the antibody chain gene while preserving the reading frame. Such a signal peptide may be represented by an immunoglobulin signal peptide or a heterologous signal peptide (i.e., a signal peptide derived from a non-immunoglobulin protein).

The recombinant expression vectors of the invention, in addition to the antibody chain genes, carry regulatory sequences that regulate the expression of the antibody chain genes in the host cell. The term "regulatory sequence" includes promoters, enhancers, and other expression control elements (e.g., polyadenylation signals) that regulate the transcription or translation of antibody chain genes. Such regulatory sequences are described, for example, in the article by Goeddel (Gene Expression Technology. Methods in Enzymology 185, Academic Press, San Diego, Calif., 1990). It should be noted that the construction of an expression vector, including the secretion of regulatory sequences, may depend on factors such as the choice of a transformable host cell, the level of expression of the desired protein, etc. Preferred sequences regulating expression in mammalian host cells include viral elements that provide for high levels of protein expression in mammalian cells, such as promoters and/or enhancers derived from cytomegalovirus (CMV), Simian virus 40 (SV40), adenovirus (for example, the adenovirus major late promoter (AdMLP)) and polyomavirus. As an alternative, non-viral regulatory sequences, such as the ubiquitin promoter or the β-globin promoter, can be used. In addition, regulatory elements consisting of sequences derived from various sources, such as the SR promoter system containing the SV40 early promoter sequences and the long terminal repeat of the human T-cell leukemia type 1 virus (Takebe, Y. et al., 1988, Mol. Cell. Biol. 8:466-472).

In addition to the antibody chain genes and regulatory sequences, the recombinant expression vectors of the invention may contain additional sequences, such as those that regulate vector replication in host cells (e.g., replication origins) and selectable marker genes. A selectable marker gene facilitates the selection of host cells into which the vector has been inserted (refer to, for example, U.S. Pat. Nos. 4,399,216, 4,634,665 and 5,179,017 patents issued to Axel et al.). For example, a selectable marker gene typically reports resistance to drugs such as G418, hygromycin or methotrexate, to host cells in which this vector has been inserted. Preferred selective marker genes include the dihydrofolate reductase (DHFR) gene (inserted into dhfr-host cells during selection/amplification using methotrexate) and the neo gene (for selection for resistance to G418).

For expression of the light and heavy chains, the expression vector(s) encoding the heavy and light chains are transferred to the host cell by standard methods. The term "transfection" in its various forms includes a wide variety of methods commonly used to insert exogenous DNA into prokaryotic or eukaryotic host cells, for example, electroporation, precipitation with calcium phosphate, transfection mediated by DEAE-dextran. Although, the antibodies of the invention can be theoretically expressed in any prokaryotic or eukaryotic host cells, eukaryotic host cells are preferred, and mammalian cells are the most preferred, since such eukaryotic cells, and in particular mammalian cells, are more suitable for "correct" assembly and secretion of an immunologically active antibody rather than prokaryotic cells. It was reported that the expression of antibody genes in prokaryotic cells was ineffective in producing high levels of an active antibody (Boss, M. A. & Wood, C. R., 1985, Immunology Today 6:12-13).

Preferred mammalian host cells suitable for expression of the recombinant antibodies of the invention include the Chinese hamster ovary cells (CHO cells) (including CHO (dhfr-) cells described in the article by Urlaub & Chasin, 1980, Proc. Natl. Acad. Sci. USA 77:4216-4220, and used with a DHFR-selective marker, for example, as described in the article by R. J. Kaufman and P. A. Sharp, 1982, Mol. Biol. 159: 601-621), NSO myeloma cells, COS cells and SP2 cells. In particular, another preferred expression system intended for use with myeloma NSO cells includes the GS gene expression system described in WO8704462, WO8901036 and EP338841. If the recombinant expression vectors encoding the antibody genes are introduced into mammalian host cells, the antibodies are produced by culturing the said host cells for a period of time sufficient to effect expression of the antibody in the said host cells, and are more preferably for the secretion of the said antibody into the culture medium in which these host cells were cultured. The antibodies can be isolated from the culture medium using standard protein purification methods.

Characterization of Antibody Binding to Antigen

Antibodies of the invention can be tested for binding to FGFR1, for example, by flow cytometry. In brief, fresh FGFR1-expressing cells are collected from tissue shake flask, and a monocellular suspension is prepared. Suspensions of the FGFR1-expressing cells are stained with the "first" antibody either directly or after fixation with 1% paraformaldehyde in PBS. Approximately one million cells are resuspended in PBS containing 0.5% BSA and 50-200 μg/mL of the "first" antibody, and then incubated on ice for 30 minutes. The cells are washed twice with PBS containing 0.1% BSA, 0.01% NaN3, resuspended in 100 μL FITC conjugate, goat anti-human IgG antibody, diluted in the ratio of 1:100 (Jackson ImmunoResearch, West Grove, Pa.), and incubated on ice for another 30 minutes. Then wash the cells again twice, resuspend in 0.5 mL wash buffer, and perform an assay for fluorescent staining on the FACSCalibur cytometer (Becton-Dickinson, San Jose, Calif.).

As an alternative, antibodies of the invention can be tested for binding to FGFR1 by standard ELISA. Briefly, the microtiter plates are coated with purified FGFR1 at a concentration of 0.25 μg/mL in PBS, and then blocked with 5% bovine serum albumin in PBS. Add antibody dilutions (for example, dilution of plasma from FGFR1-immunized mice) to each well and incubate for 1 to 2 hours at 37° C. Wash the plates with PBS/Tween and then incubate with the "second" antibody (e.g., for human antibodies, with goat polyclonal Fc-specific anti-human IgG antibody) conjugated to alkaline phosphatase, for 1 hour at 37° C. After washing, add pNPP substrate (1 mg/mL) to the plates for the development of staining and test at $OD_{405-650}$. It is usually preferable to use a mouse, in which the greatest antibody titers are produced, for the cell fusion.

For hybridoma screening, which show a positive reactivity with the FGFR1 immunogen, the aforesaid ELISA or FACS assays can also be performed. Subclone hybridomas that bind to FGFR1 with high avidity, and then evaluate them. One clone from each hybridoma that retains the reactivity of the parent cells (as indicated by ELISA or FACS) can be selected to create a cell bank in 5-10 vessels that are stored at −140° C. and used to purify antibodies.

To purify anti-FGFR1 antibodies, the selected hybridomas can be cultured in two-liter centrifuge flasks designed to purify monoclonal antibodies.

Supernatants can be filtered and concentrated, and then subjected to affinity chromatography on protein A-Sepharose (Pharmacia, Piscataway, N.J.). To ensure the desired purity, eluted IgG can be assessed by gel electrophoresis and high performance liquid chromatography. The buffer solution can be replaced with PBS, and the concentration can be determined by $OD_{280}$ using an extinction coefficient of 1.43. Monoclonal antibodies can be divided into aliquots and stored at −80° C.

To determine whether the selected monoclonal anti-FGFR1 antibodies bind to unique epitopes, each antibody can be biotinylated using commercially available reagents (Pierce, Rockford, Ill.). Competitive binding studies using unlabeled monoclonal antibodies and biotinylated monoclonal antibodies can be performed on the aforesaid FGFR1-sensitized ELISA plates. The binding of the biotinylated mAb can be detected using streptavidin-alkaline phosphatase as a probe. As an alternative, competitive binding studies can be performed using a radiolabeled antibody, and unlabeled competing antibodies can be detected by the Scatchard analysis.

To determine the isotype of purified antibodies, ELISA isotype antibody assays can be performed using reagents specific for antibodies of a particular isotype. For example, to determine the isotype of a human monoclonal antibody, microtiter plate wells are coated with 1 μg/mL anti-human immunoglobulin antibody and allowed to stand overnight at 4° C. After blocking with 1% BSA, the plates are caused to react with 1 μg/mL or less of the monoclonal antibodies tested or purified isotype control antibodies at room temperature for 1-2 hours. The wells can then be caused to react with antibody probes specific for human IgG1 or human IgM and conjugated to alkaline phosphatase. The plates are developed and analysed as described above.

Physical Properties of Antibodies

The anti-FGFR1 antibodies of the invention can also be characterized by various physical properties. Different classes of such antibodies can be identified and/or determined on the basis of their physical properties using various assays.

In some embodiments, the antibodies may comprise one or more glycosylation sites in the light or heavy chain variable region. The presence of one or more glycosylation sites in the variable region may result in increased immunogenicity of the antibody, or in the change in antibody pK, caused by changes in binding to the antigen (Marshall et al., 1972, Annu. Rev. Biochem. 41:673-702; Gala F. A. & Morrison S. L., 2004, J. Immunol. 172:5489-94; Wallick et al., 1988, J. Exp. Med. 168:1099-109; Spiro R. G., 2002, Glycobiology 12:43R 56R; Parekh et al., 1985, Nature 316:452-7: Mimura et al., 2000, Mol. Immunol. 37:697-706). It is known that glycosylation occurs in motifs containing the N-X-S/T sequence. Glycosylation of the variable region can be tested using the glycoblotting technique, where the test antibody is split to produce a Fab fragment, and then tested for glycosylation using an assay in which the level of periodate oxidation and the formation of Schiff bases are determined. As an alternative, the glycosylation of the variable region can be tested by chromatography (Dionex-LC) with light scattering measurement, where the Fab saccharides are split to monosaccharides, and analyzed for the content of the individual saccharides. In some cases, it is preferable for anti-FGFR1 antibody to contain no glycosylation sites in the variable region. This can be achieved either by selecting antibodies that do not contain the motif of glycosylation in the variable region, or by mutation of the residues in the motif of glycosylation using standard methods well known to those skilled in the art.

Each antibody has a unique isoelectric point (pi), but the antibody typically has pl at the pH range of 6-9.5. The pl for the IgG1 antibody is usually within the pH range of 7-9.5, and pl for the IgG4 antibody is usually within the pH range of 6-8. Antibodies can have pl that goes beyond the specified interval. Although the effect of such pl values is substantially unknown, it is believed that antibodies with a pl value that is outside the normal ranges may have some degree of unfolding and instability in in vivo conditions. The isoelectric point can be determined by a capillary isoelectric focusing method in which a pH gradient is created, and laser focusing can be used for the greater accuracy (Janini et al., 2002, Electrophoresis 23: 1605-11; Ma et al., 2001, Chromatographia 53: S75-89; Hunt et al., 1998, J. Chromatogr A 800:355-67). In some cases, the anti-FGFR1 antibody is preferred to have a pl value within the normal range. This can be achieved either by selecting antibodies with pl within the normal range or by mutating the charged surface residues using standard techniques well known to those skilled in the art.

Each antibody has a melting point, which is an indicator of its thermal stability (Krishnamurthy R. & Manning M. C., 2002, Curr. Pharm. Biotechnol. 3:361-71). The higher the antibody thermal stability is, the higher its overall in vivo stability is. The melting point of the antibody can be measured by standard methods, such as differential scanning calorimetry (Chen et al., 2003, Pharm. Res. 20:1952-60; Ghirlando et al., 1999, Immunol. Lett. 68:47-52). TM1 means the temperature of the initial antibody unfolding. TM2 means the temperature of the full antibody unfolding. The TM1 of the antibody of the invention usually preferably exceeds 60° C., more preferably exceeds 65° C., and even more preferably exceeds 70° C. As an alternative, the antibody thermal stability can be measured using circular dichroism (Murray et al., 2002, J. Chromatogr Sci. 40:343-9). In a preferred embodiment of this invention, those antibodies are selected which decompose slowly enough. Fragmentation of the anti-FGFR1 antibody can be measured using capillary electrophoresis (CE) and MALDI-MS methods well known to those skilled in the art (Alexander A. J. and Hughes, D. E., 1995, Anal. Chem. 67:3626-32). In another preferred embodiment, those antibodies are selected which are subject to minimal aggregation. Aggregation can cause undesirable immune response and/or production of altered or adverse pharmacokinetic properties. Generally acceptable antibodies include those antibodies which aggregation is 25% or less, preferably is 20% or less, even more preferably is 15% or less, even more preferably is 10% or less, and most preferably is 5% or less. Aggregation can be measured by various methods well known to those skilled in the art, including column chromatography (SEC/GPC), high performance liquid chromatography (HPLC), and a light scattering method for characterizing monomers, dimers, trimers or multimers.

Immunoconjugates

In another aspect, this invention relates to an anti-FGFR1 antibody or its fragment conjugated to a therapeutic molecule, such as a cytotoxin, a drug (e.g., an immunosuppressant) or a radiotoxin. Such conjugates are referred to herein as "immunoconjugates". Immunoconjugates, which include one or more cytotoxins, are called "immunotoxins". The cytotoxin or cytotoxic agent includes any agent that has a negative effect on the cell (e.g., destroys the cell). The examples include taxol, cytochalasin B, gramicidin D, ethidium bromide, emetine, mitomycin, etoposide, tenoposide, vincristine, vinblastine, colchicine, doxorubicin, daunorubicin, dihydroxyanthracyndione, mitoxantrone, mitramycin, actinomycin D, 1-dehydrotestosterone, glucocorticoids, procaine, tetracaine, lidocaine, propranolol and puromycin, and analogs or homologs thereof. Therapeutic agents do also include, for example, antimetabolites (for example, methotrexate, 6-mercaptopurine, 6-thioguanine, cytarabine, 5-fluorouracylldecarbazine), alkylating agents (e.g., mechlorethamine, thiotepa, chlorambucil, melphalan, carmustine (BSNU) and lomustine (CCNU), cyclophosphamide, busulfan, dibromannite, streptozotocin, mitomycin C and cis-dichlorodiamine platinum (II) (DDP), i.e. cisplatin), anthracyclines (for example, daunorubicin (previous name: daunomycin) and doxorubicin), antibiotics (for example, dactinomycin (previous name: actinomycin), bleomycin, mitramycin and anthramycin (AMC)) and antimitotic agents (e.g., vincristine and vinblastine).

Other preferred examples of therapeutic cytotoxins that can be conjugated to the antibody of the invention include duocarmicin, calicheamicin, maytansine and auristatin, and derivatives thereof. For example, the "calicheamicin antibody" conjugate is commercially available (Mylotarg®; Wyeth-Ayerst).

Cytotoxins can be conjugated to antibodies of the invention using a linker technology known to those skilled in the art. Examples of linkers that can be used to conjugate a cytotoxin to an antibody include, but are not limited to, linkers containing hydrazones, thioethers, esters, disulfides, and peptides. For example, a linker that is sensitive to cleavage at a low pH in a lysosomal compartment or a protease-sensitive linker, such as proteases predominantly expressed in tumor tissue, such as cathepsins (e.g., cathepsins B, C, D), can be selected.

A more detailed discussion of cytotoxin, linker types and methods of conjugating therapeutic agents with antibodies can also be found in the articles by Saito, G. et al., 2003, Adv. Drug Deliv. Rev. 55:199-215; Trail, P. A. et al., 2003, Cancer Immunol. Immunother. 52:328-337; Payne, G., 2003, Cancer Cell 3:207-212; Allen, T. M., 2002, Wat. Rev. Cancer 2:750-763; Pastan, I. and Kreitman, R. J., 2002, Curr. Opin. Investig. Drugs 3:1089-1091; Senter, P. D. и Springer, C. J., 2004, Adv. Drug Deliv. Rev. 53:247-264.

Antibodies of the invention can also be conjugated to a radioactive isotope to produce cytotoxic radiopharmaceuticals, also called radioimmunoconjugates. Examples of radioactive isotopes that can be conjugated to antibodies intended for use in diagnosis or treatment include, but are not limited to, iodine-131, iodine-125, indium-111, yttrium-90 and lutetium-177. The radioimmunoconjugates production method is well developed by persons skilled.

Examples of radioimmunoconjugates include commercially available radioimmunoconjugates, including Zevalin® (IDEC Pharmaceuticals) and Bexxar® (Corixa Pharmaceuticals), and similar methods can be used to produce radioimmunoconjugates using the antibodies of the invention.

The antibody conjugates of the invention can be used to modify this biological response, and the choice of drug need not necessarily be limited to classical chemical therapeutic agents. Thus, for example, the said drug may be represented by a protein or a polypeptide with the necessary biological activity. Such proteins can include, for example, an enzymatically active toxin or an active fragment thereof, such as abrin, ricin A, *Pseudomonas* exotoxin or diphtheria toxin; a protein such as tumor necrosis factor or interferon; or biological response modifiers such as, for example, lymphokines, interleukin-1 (IL-1), interleukin-2 (IL-2), interleukin-6 (IL-6), granulocyte-macrophage colony stimulating factor (GM-CSF), granulocyte colony-stimulating factor (G-CSF) or other growth factors. Methods of conjugating such therapeutic agents to antibodies are well known to those skilled in the art, refer, for example, to the article by Arnon et al., "Monoclonal Antibodies for Immunotargeting of Drugs in Cancer Therapy," Monoclonal Antibodies and Cancer Therapy, Reisfeld et al. (eds.), pp. 243-56 (Alan R. Liss, Inc. 1985); Hellstrom et al, "Antibodies For Drug Delivery," Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review," in Monoclonal Antibodies '84: Biological and Clinical Applications, Pinchera et al. (eds.), pp. 475-506, 1985; "Analysis, Results and Future Prospective of The Therapeutic Use Of Radiolabeled Antibody In Cancer Therapy," in Monoclonal Antibodies For Cancer Detection and Therapy, Baldwin et al. (eds.), pp. 303-16 (Academic Press 1985) ii Thorpe et al., "The Preparation and Cytotoxic Properties Of Antibodiy-Toxin Conjugates," Immunol. Rev., 62:119-58, 1982.

Bispecific Molecules

In another aspect, this invention relates to bispecific molecules comprising an anti-FGFR1 antibody of the invention or a fragment thereof. The antibody of the invention or its antigen-binding segment may be derivatised or linked to another functional molecule, for example, to another peptide or protein (e.g., to another antibody or receptor) to produce a bispecific molecule that binds to at least two different binding sites or target molecules. The antibody of the invention can be in fact derivatised or linked to more than one other functional molecule to produce multispecific molecules that bind to more than two different binding sites and/or to target molecules; and such multispecific molecules are also included in the definition of the term "bispecific molecule" as used herein. To create a bispecific molecule of the invention, the antibody of the invention can be functionally linked (e.g., by chemical binding, gene binding, non-covalent binding, or any other binding method) to one or more other binding molecules, such as another antibody, antibody fragment, peptide or binding mimetic, to obtain the desired bispecific molecule. Pursuant thereto, this invention includes bispecific molecules with at least one first binding specificity to FGFR1 and the second binding specificity to the second target epitope. In a particular embodiment, an Fc receptor, for example, human FcγRI, is the said second target epitope. Therefore, this invention includes bispecific molecules capable of binding to FcγRI-expressing effector cells (e.g., monocytes, macrophages or polymorphonuclear cells (PMNCs)) and to target cells expressing FGFR1. Such bispecific molecules deliver the FGFR1-expressing cells to excitatory cells and stimulate the Fc receptor-mediated activity of excitatory cells, such as phagocytosis of FGFR1-expressing cells, antibody-dependent cell-mediated cytotoxicity (ADCC), cytokine release, or formation of superoxide anion. In an embodiment where the bispecific molecule is a multispecific one, the said molecule in addition to Fc binding specificity and FGFR1 binding specificity may further have a third binding specificity. In one embodiment, an anti-stimulatory factor (EF) region features such a third binding specificity, for example, a molecule that binds to a surface protein involved in cytotoxic activity and thereby enhances an immune response against the target cell. Such an "anti-stimulatory factor" region may be represented by an antibody, a functional antibody fragment or a ligand that binds to a given molecule, for example an antigen or receptor, and thereby enhances the binding of epitopes to the Fc receptor or target cell antigen. Such an "anti-stimulatory factor" region can bind to the Fc receptor or antigen of a target cell. As an alternative, the "anti-stimulatory factor" region can bind to a molecule that is different from the molecule to which regions with the first and second binding specificity bind. For example, a segment of the anti-stimulatory factor antibody may bind to a cytotoxic T-cell (e.g., via CD2, CD3, CD8, CD28, CD4, CD40, ICAM-1 or other immune cells), which leads to an increase in the immune response against the target cell. In one embodiment, the said bispecific molecules of the invention comprise at least one antibody or fragment thereof as a molecule having binding specificity, including, for example, Fab, Fab', F (ab') 2/Fv, Fd, dAb or single-chain Fv. The specified antibody can also be a light chain or heavy chain dimer, or any minimal fragment thereof, such as Fv, or a single-chain construct described in U.S. Pat. No. 4,946,778, Ladner et al. In one embodiment, the binding specificity to the Fc receptor is provided by a monoclonal antibody, which binding is not blocked by human immunoglobulin (IgG). The term "IgG receptor" as used herein means any of the eight genes encoding the γ-chain and localized on chromosome 1. These genes encode only twelve transmembrane or soluble isoforms of the receptor, which are subdivided into three classes of Fcγ receptors: FcγRI (CD64), FcγRII (CD32) and FcγRIII (CD16). In one preferred embodiment, the Fcγ receptor is represented by the human high-affinity FcγRI. Human FcγRI is a 72-kDa molecule that has a high affinity for monomeric IgG ($10^8$-$10^9$ M-1). The production and characterisation of some preferred monoclonal anti-Fcγ antibodies is described in WO 88/00052, Fanger et al., as well as in the U.S. Pat. No. 4,954,617 patent. These antibodies bind to the FcγRI, FcγRII or FcγRIII epitope at a site that is different from the Fcγ binding site of the said receptor, and therefore their binding is not substantially blocked by IgG at the physiological level.

In yet another preferred embodiment, the binding specificity to the human Fc receptor is provided by an antibody that binds to an IgA receptor, for example, an Fcα receptor (FcαRI, CD89), which binding is preferably not blocked by human immunoglobulin A (IgA). The term "IgA receptor" as used herein means any gene product encoded by a single α-gene (FcαRI) located on chromosome 19. It is known that this gene encodes several 55-110 kDa alternatively spliced transmembrane isoforms. FcαRI (CD89) is constitutively expressed on monocytes/macrophages, eosinophil and neutrophil granulocytes, but not on populations of non-excitatory cells. FcαRI has an average affinity ($5 \times 10^7$ M-1) for both IgA1 and IgA2, which is increased when exposed to cytokines such as G-CSF or GM-CSF (Morton, H C et al., 1996, Critical Reviews in Immunology 16: 423-440). Four FcαRI-specific monoclonal antibodies identified as antibodies A3, A59, A62 and A77 that bind to the FcαRI receptor located outside the domain bound to the IgA ligand, were described (Monteiro, R. C. et al., 1992, J. Immunol. 148: 1764). FcγRI and FcαRI are the preferred stimulating receptors used in the bispecific molecules of the invention, since they (1) express mainly on immune effector cells, for example monocytes, PMN, macrophages and dendritic cells; (2) express at high levels (e.g., 5000-100000 per cell); (3) are mediators of cytotoxic activity (e.g., ADCC, phagocytosis) and (4) mediate an elevated level of antigen presentation, including autoantigens targeting them. Although human monoclonal antibodies are preferred, other antibodies that are murine, chimeric and humanized monoclonal antibodies can also be used in the bispecific molecules of the invention. The bispecific molecules of the invention can be produced by conjugation of molecules with binding specificity, for example, to FcR and FGFR1, by methods known to those skilled in the art. For example, each bispecific molecule with binding specificity can be produced separately, and then all these molecules can be conjugated to each other. If molecules with binding specificity are represented by proteins or peptides, a number of binding or crosslinking agents can be used for covalent binding. Examples of crosslinking agents include protein A, carbodiimide, N-succinimidyl-3-acetyl-thioacetate (SATA), 5,5'-dithiobis (2-nitrobenzoic acid) (DTNB), o-phenylene dimaleimide (oPDM), N-succinimidyl-3-(2-pyridyldithio) propionate (SPDP) and sulfosuccinimidyl-4-(N-maleimidomethyl)cyclohexane-1-carboxylate (Sulfo-SMCC) (refer to, for example, Karpovsky et al., 1984, J. Exp. Med. 160:1686; Liu, M A et al., 1985, Proc. Natl. Acad. Sci. USA 82:8648). Other methods include methods described by Paulus, 1985, Behring Ins. Mitt. No. 78, 118-132; Brennan et al., 1985, Science 229:81-83 and Glennie et al., 1987, J. Immunol. 139:2367-2375. Preferred conjugating agents include SATA and sulfo-SMCC, supplied by Pierce Chemical Co. (Rockford, Ill.). If the specific binding molecules are represented by antibodies, they can be conjugated via a sulfhydryl linkage to the C-terminal hinge regions of two heavy chains. In a particular preferred embodiment, the hinge region should modified in such a manner that it contains an odd number of sulfhydryl residues, and preferably one residue, and then conjugation should be performed. As an alternative, both specific binding molecules can be encoded in the same vector and can express and be assembled in the same host cell. This method is particularly suitable in the case when the bispecific molecule is represented by a fusion protein, mAb-mAb, mAb-Fab, Fab-F(ab') 2, or Fab ligand. The bispecific molecule of the invention can be represented by a single-stranded molecule containing a single-chain antibody and a binding determinant, or a single-stranded bispecific molecule containing two binding determinants. Bispecific molecules can contain at least two single-stranded molecules. Bispecific molecule production methods are described, for example, in U.S. Pat. No. 5,260, 203; in U.S. Pat. No. 5,455,030; in U.S. Pat. No. 4,881,175; in U.S. Pat. No. 5,132,405; in U.S. Pat. No. 5,091,513; in U.S. Pat. No. 5,476,786; in U.S. Pat. No. 5,013,653; in U.S. Pat. No. 5,258,498 and in U.S. Pat. No. 5,482,858. The binding of bispecific molecules to their specific targets can be confirmed, for example, by enzyme immunoassay (ELISA), radioimmunoassay (RIA), FACS analysis, bioassay (e.g., for growth inhibition) or western blotting. In each of these assays, the presence of the protein antibody complexes of particular interest is usually detected using a labeled reagent (e.g., an antibody) specific for the complex of interest. For example, FcR antibody complexes can be detected using, for example, an enzyme-linked antibody or antibody fragment that identifies the said "antibody-FcR" complexes and specifically binds thereto. Alternatively, such complexes can be detected by any of a number of other immunoassays. For example, an antibody can be radiolabeled and can be used in radioimmunoassay (RIA) (refer to, for example, an article by Weintraub, B., Principles of Radioimmunoassays, Seventh Training Course on Radioligand Assay Techniques, The Endocrine Society, March, 1986). A radioactive isotope can be detected by a γ-counter or a scintillometer, or by autoradiography.

Pharmaceutical Compositions

In another aspect, this invention relates to a composition, for example, to a pharmaceutical composition comprising one monoclonal antibody of the invention or antigen binding the section(s) or combinations thereof in combination with a pharmaceutically acceptable carrier. Such compositions may comprise one antibody or combinations thereof (e.g., two or more different antibodies), or immunoconjugates, or bispecific molecules of the invention. For example, the pharmaceutical composition of the invention can comprise a combination of antibodies (or immunoconjugates, or bispecific molecules) binding to different epitopes on the target antigen or having additional activity. The pharmaceutical compositions of the invention can also be used in combined therapy, i.e. they can be administered in combination with other agents. For example, the combined therapy may include the administration of an anti-FGFR1 antibody of the invention in combination with at least one other anti-inflammatory or immunosuppressive agent. Examples of therapeutic agents that can be used in combined therapy are described in further detail in the section on the use of antibodies of the invention below. The term "pharmaceutically acceptable carrier" as used herein includes any and all physiologically-compatible solvents, dispersive materials, coating materials, antibacterial and antifungal agents, isotonic agents, and absorption inhibitors, etc. Such carrier is usually represented by a carrier suitable for intravenous, intramuscular, subcutaneous, parenteral, intraspinal or intradermal administration (e.g., by injection or infusion). Depending on the administration route, the active compound, i.e., the antibody, immunoconjugate or bispecific molecule, may have a coating of a material protecting the compound from the effects of acids and other environmental conditions that can inactivate this compound. The pharmaceutical compounds of the invention may include one or more pharmaceutically acceptable salts. The term "pharmaceutically acceptable salt" means a salt that maintains the desired biological activity of the parent compound and has no adverse toxic effect (refer to, for example, Berge, S. M., et al., 1977, J. Pharm. Sci. 66:1-19). Examples of such salts include acid addition salts and base addition salts. Acid addition salts are salts derived from nontoxic inorganic acids such as hydrochloric, nitric, phosphoric, sulfuric, hydrobromic, hydroiodic, phosphoric acids, etc., as well as from non-toxic organic acids such as aliphatic mono- and dicarboxylic acids, phenyl substituted alkanoic acids, hydroxyalkanoic acids, aromatic acids, aliphatic and aromatic sulfonic acids, etc. The base addition salts are salts derived from alkaline earth metals such as sodium, potassium, magnesium, calcium, etc., as well as from non-toxic organic amines such as N,N'-dibenzylethylenediamine, N-methylglucamine, chlorprocarin, choline, diethanolamine, ethylenediamine, procaine, etc. The pharmaceutical composition of the invention may also include a pharmaceutically acceptable antioxidant. Examples of pharmaceutically acceptable antioxidants include: (1) water-soluble antioxidants such as ascorbic acid, cysteine hydrochloride, sodium bisulfate, sodium metabisulphite, sodium sulfite, etc.; (2) oil-soluble antioxidants such as ascorbyl palmitate, butylated hydroxyanisole (BHA), butylated hydroxytoluene (BHT), lecithin, propyl gallate, α-tocopherol, etc.; and (3) metal chelating agents, such as citric acid, ethylenediaminetetraacetic acid (EDTA), sorbitol, tartaric acid, phosphoric acid, etc.

Examples of suitable aqueous and anhydrous carriers that can be used in the pharmaceutical compositions of the invention include water, ethanol, polyols (such as glycerol, propylene glycol, polyethylene glycol, etc.) and suitable mixtures thereof, vegetable oils such as olive oil, and organic esters for injection, such as ethyl oleate. The desired fluidity can be maintained, for example, by coating with materials such as lecithin, by maintaining the desired particle size in the case of dispersions, and by using surfactants. These compositions may also contain adjuvants such as preservatives, wetting agents, emulsifying agents and dispersing agents. Protection against microorganisms can be achieved, for example, by sterilization or by incorporating various antibacterial and antifungal agents, for example, paraben, chlorobutanol, phenol-sorbic acid, etc. It may also be desirable to include isotonicity agents, such as sugars, sodium chloride, etc., into the composition. In addition, prolonged absorption of the pharmaceutical preparation for injection can be achieved by including absorption inhibitors, such as aluminum monostearate and gelatin. The pharmaceutically acceptable carriers include sterile aqueous solutions or dispersions, and sterile powders for the quick preparation of sterile solutions or dispersions for injection. The use of such media and agents for the preparation of pharmaceutically active compounds is known to those skilled in the art. Any standard media or agents can be used in the pharmaceutical compositions of the invention, with the exception of those that are incompatible with this active compound. Additional active compounds can also be added to such compositions. The therapeutic compositions should be sterile and stable under their preparation and storage conditions. Such compositions may be formulated as a solution, microemulsion, liposome or other well-ordered structures suitable for achieving high drug concentrations. The carrier may be represented by a solvent or dispersion medium containing, for example, water, ethanol, polyol (e.g., glycerin, propylene glycol and liquid polypropylene glycol, etc.) and suitable mixtures thereof. The desired fluidity can be maintained, for example, by coating with materials such as lecithin, by maintaining the desired particle size in the case of dispersions, and by using surfactants.

Sterile solutions for injections can be prepared by adding the active compound to the appropriate solvent in the required amount, taken either alone or in combination with the aforesaid ingredients, if necessary, followed by microfiltration by sterilisation. Dispersions are usually produced by adding the active compound to a sterile carrier containing a base dispersion medium and other necessary ingredients listed above. In the case of sterile powders for the preparation of sterile solutions for injections, the preferred methods for preparing such preparations include vacuum drying and freeze drying (lyophilisation), which results in a powder consisting of the active ingredient and any other desired ingredient obtained from the said sterile prefiltered solution.

The amount of active ingredient that can be combined with the carrying agent for the preparation of a single dosage form may vary depending on the treated subject and on the particular administration route. The amount of active ingredient that can be combined with the carrying agent to produce a single dosage form is usually the found amount that produces a therapeutic effect. Such amount, on the base of 100% of the total amount of the composition, is in general in the range of about 0.01 to 99% of the active ingredient, preferably about 0.1 to 70%, and most preferably about 1 to 30% of the active ingredient in combination with a pharmaceutically acceptable carrier. The dosage regimen is selected so that the optimal desired response is achieved (e.g., a therapeutic response). Thus, for example, a single loading dose or several divided doses may be administered over a period of time, or this dose may be prosegmentally reduced or increased depending on therapeutic indications.

To facilitate the administration and to ensure uniform administration of doses, a unit dosage form is a particularly preferred composition for parenteral administration. The term "unit dosage form" as used herein means a physically discrete unit suitable for a single dose administration to a treated subject; provided that each such unit contains a predetermined amount of the active compound necessary to achieve the desired therapeutic effect in combination with a suitable pharmaceutical carrier. The specification of unit dosage forms of the invention is determined by such factors and directly depends on such factors as (a) the unique properties of the active compound, and the specifically achieved therapeutic effect, and (b) the limitations encountered by those skilled in the art when preparing such an active compound and which are associated with susceptibility of the patient to the treatment used. Doses of the administered antibody are in the range of about 0.0001 to 100 mg/kg, and usually are from 0.01 to 25 mg/kg body weight of the host. For example, these doses may be 0.3 mg/kg body weight, 1 mg/kg body weight, 3 mg/kg body weight, 5 mg/kg body weight or 10 mg/kg body weight, or in the range from 1 to 10 mg/kg. If necessary, higher doses may be administered, for example, 15 mg/kg body weight, 20 mg/kg body weight or 25 mg/kg body weight.

A representative treatment regimen provides for the administration of a dose once a week, once every two weeks, once every three weeks, once every four weeks, once a month, once every 3 months, or once every 3-6 months. A preferred dose schedule for the antibody of the invention provides for intravenous administration of 1 mg/kg body weight or 3 mg/kg body weight, wherein the said antibody is injected according to one of the following dose schedules: (i) every four weeks, 6 doses, and then every three months; (ii) every three weeks; (iii) one dose of 3 mg/kg body weight, and then one dose of 1 mg/kg body weight every three weeks.

In some methods, two or more monoclonal anti-FGFR1 antibodies of the invention are injected with different binding specificities simultaneously, and in this case the dose of each antibody administered is within the stated range. The antibody is generally injected in multiple doses. Single doses can be injected at intervals of once a week, once a month, every three months or once a year. The dosage intervals may also be irregular and may be set according to the measured levels of the antibody against the target antigen in the patient's blood. In some methods, the doses may be adjusted to achieve antibody plasma concentration in the range of about 1-1000 µg/mL, and in some methods, about 25-300 µg/mL. In other methods, one or more monoclonal anti-FGFR1 antibodies of the invention are injected simultaneously with an antibody with another binding specificity, for example, with an antibody such as an anti-CTLA-4 antibody and/or an anti-PD-1 antibody, and in this case, each antibody is injected at a dose the amount of which is within the set ranges. Alternatively, the antibody can be injected as an extended release drug, and in this case, less frequent injections are required. The injection dose and frequency vary depending on the antibody half-life in the patient's body. In general terms, human antibodies have the longest half-life, followed by humanized antibodies, chimeric antibodies and non-human antibodies. The injection dose and frequency may vary depending on whether the treatment is prophylactic or therapeutic. In case of prophylactic use, a relatively low antibody dose is injected at relatively large intervals over a long period of time. Some patients undergo lifelong treatment. In case of therapeutic use, a relatively high dose sometimes might be injected at relatively short intervals to slow or stop the disease progression, and, preferably, until the patient has a partial relief or complete subsidence of the disease symptoms. Then the preventive treatment can be prescribed to the patient. The actual doses of the active ingredients in the pharmaceutical compositions of the invention can be varied in order to obtain the active ingredient amount that is effective to achieve the desired therapeutic response in a given patient with the appropriate composition formulation and the appropriate administration route, and which has no toxic effect on the patient. The dose selection depends on a number of pharmacokinetic factors, including the activity of the particular compositions of the invention or their esters, salts or amides, the administration route, the time of administration, the clearance rate of the particular compound used, the treatment duration, the presence of other drugs, compounds and/or substances, used in combination with these compositions, as well as on the age, sex, body weight, disease severity, general health status and medical history of the treated patient, and from other factors well known to medical specialists.

The "therapeutically effective dose" of the anti-FGFR1 antibody of the invention generally provides for the reduction the severity of the disease symptoms, the increase in the frequency and duration of remission, or the preventing of the deterioration in condition or disability caused by the disease. For example, for the treatment of FGFRR+ tumors, the "therapeutically effective dose" does preferably inhibit the growth of cells or tumors by at least about 20%, more preferably—at least about 40%, even more preferably—at least about 60%, and most preferably—at least about 80% compared to untreated patients. The ability of a compound to inhibit tumor growth can be evaluated in an animal with a predictable model of active growth of human tumors. Alternatively, this property of the composition can be assessed by determining the ability of a given compound to inhibit tumor growth, where such in vitro inhibition is performed using tests known to those skilled in the art. The therapeutically effective dose of the therapeutic compound can help to reduce the tumor size or to relieve any other symptoms of the patient. The average person skilled in the art can independently determine the desired amounts based on factors such as the patient's body weight, his/her symptoms burden, the particular composition formulation, or the chosen administration route. The composition of the invention can be injected by one or more routes according to a procedure well known to those skilled in the art. As is known to those skilled in the art, the route and/or mode of administration may vary depending on the desired results. Preferred routes for administering the antibodies of the invention include intravenous, intramuscular, intradermal, intraperitoneal, subcutaneous and intraspinal administration or other methods of parenteral administration, for example, by injection or infusion. The term "parenteral administration" as used herein means administration routes other than intestinal and topical administration, usually performed by injection, and such methods include, but are not limited to, intravenous, intramuscular, intraarterial, intrathecal, intracapsular, intraorbital, intracardiac, intradermal, intraperitoneal, transtracheal, subcutaneous, subepidermal, intraarticular, subcapsular, subarachnoid, intraspinal, epidural and intrasternal injections and infusions. Alternatively, the antibody of the invention can be administered by non-parenteral administration, such as topical or transepidermal administration or mucosal administration, for example, by intranasal, oral, vaginal, rectal, sublingual or topical administration route.

The active compounds can be produced in combination with carriers that protect the compound from rapid release, for example, they can be formulated as a controlled-release preparation, including implants, transdermal patches, and microencapsulation. Biodegradable and biocompatible polymers such as ethylene vinyl acetate, polyanhydrides, polyglycolic acid, collagen, polyorthoesters, and polylactic acid may be used. Many preparation techniques for such compounds have been patented or are essentially known to those skilled in the art. Refer to, for example, Sustained and Controlled Release Drug Delivery Systems, J. R. Robinson, ed., Marcel Dekker, Inc., New York, 1978. Therapeutic compositions can be administered using medical equipment known to those skilled in the art. For example, in a preferred embodiment of the invention, the therapeutic composition of the invention can be administered using a needleless hypodermic injection system, such as those described in U.S. Pat.

Nos. 5,999,163; 5,383,851; 5,312,335; 5,064,413; 4,941,880; 4,790,824 or 4,596,556. Examples of well-known implants and modules used in this invention can be found in U.S. Pat. No. 4,487,603, which describes an implantable microinfusion pump for administering a drug at a controlled rate; in U.S. Pat. No. 4,486,194, which describes a therapeutic device for transdermal drug administration; in U.S. Pat. No. 4,472,033, which describes a medical infusion pump for the drug administration at a predetermined infusion rate; in U.S. Pat. No. 4,472,224, which describes an implantable device for the continuous drug infusion at different flow rates; in U.S. Pat. No. 4,439,196, which discloses an osmotic drug delivery system with multichamber compartments; and U.S. Pat. No. 4,475,196, which describes an osmotic drug delivery system. These patents are incorporated herein by reference. Many other similar implants, delivery systems and modules are known to those skilled in the art.

In some embodiments, the human monoclonal antibodies of the invention can be produced in such a manner so that they have an appropriate in vivo distribution. For example, the blood-brain barrier (BBB) does not flow many highly hydrophilic compounds. To allow the therapeutic compounds of the invention to flow trough the BBB (if necessary), they can be produced, for example, in the form of liposomes. Methods for the liposome preparation are described, for example, in U.S. Pat. Nos. 4,422,811; 5,374,548 and 5,399,331. Liposomes can comprise one or more molecules that are selectively transported to specific cells or organs, which increases the efficacy of directed drug delivery (refer to, for example, V. V. Ranade, 1989, J. Clin. Pharmacol. 29:685). Representative targeting molecules are represented by folate or biotin (refer to, for example, U.S. Pat. No. 5,416,016, Low et al.); mannosides (Umezawa et al., 1988, Biochem. Biophys. Res. Commun. 153:1038); antibodies (P. G. Bloeman et al., 1995, FEBS Lett. 357:140; M. Owais et al., 1995, Antimicrob. Agents Chemother. 39:180); surfactant protein a receptor (Briscoe et al., 1995, Am. J. Physiol. 1233: 134); p 120 (Schreier et al., 1994, J. Biol. Chem. 269:9090): See also K. Keinanen; M. L. Laukkanen, 1994, FEBS Lett. 346:123; J. J. Killion; L. J. Fidler, 1994, Immunomethods 4:273.

Use and Methods of the Invention

Antibodies, and in particular, humanized antibodies, antibody compositions and methods of the invention can be used in vitro and in vivo for various diagnostic and therapeutic purposes, for example, for detecting FGFR1, for treatment oncological diseases or for enhancing the immune response by blocking FGFR1. In a preferred embodiment, human antibodies are the antibodies of the invention. For example, these molecules can be injected into a cell culture, either in vitro or ex vivo, or a human, for example, in vivo, to treat, prevent and diagnose various disorders, or to improve immunity under different conditions. The term "individual" as used herein includes both a human and an animal. Such animals are represented by all vertebrates, for example mammals and non-mammals such as non-human primates, sheep, dogs, cats, cows, horses, chickens, amphibians and reptiles. The preferred individual is a human, namely, a patient suffering from disorders associated with the FGFR1 expression, or in need of an improvement of the immune response. The aforesaid methods are particularly suitable for the treatment of a person suffering from a disorder associated with a failure of the FGFR1 expression. Such methods are also particularly suitable for the treatment of a person suffering from a disorder that can be treated by increasing the level of the T-cell-mediated immune response. To improve an antigen-specific immune response, anti-FGFR1 antibodies can be administered together with the antigen of interest. If anti-FGFR1-antibodies are administered together with another agent, these two components can be administered either sequentially or simultaneously. In view of the fact that the antibody of the invention specifically binds to FGFR1, it should be noted that the antibodies of the invention can be used to specifically detect the FGFR1 expression on the cell surface and, in addition, they can be used to isolate FGFR1 by immunoaffinity chromatography.

Malignant Tumors

FGFR1 is expressed in various human malignant tumors, including non-small cell lung cancer, breast cancer, stomach and esophageal cancers, prostate cancer, bladder cancer, head and neck cancer, melanoma (C. Behrens et al. J Clinical cancer research 14, 19, 2008; M. Koziczak et al. J Oncogene, 23, 20, 2004; K. Freier J Oral Oncology 43, 1, 2007; E. Shin et al. J Cancer Res Clin Oncol. 126, 9, 2000; K. Sugiura et al. J Oncology reports 17, 3, 2007; E. Devilard et al. J BMC Cancer 6, 272, 2006; G. Lefèvre et al. J Investigative Ophthalmology and Visual Science 50, 2009).

The anti-FGFR1 antibody itself can be used to inhibit tumor growth. Alternatively, the anti-FGFR1 antibody can be used in combination with other immunogenic agents, with standard anticancer therapy or with other antibodies described below. The FGFR1 expression in patients with renal cell carcinoma (RCC) was detected in the studies performed (KCRB-L01, WO2011000384). Immunohistochemistry analysis was performed on slices of paraffin blocks of tumors in 140 patients with RCC. The findings obtained were compared with the FGFR1 expression in 40 healthy donors who previously had kidney biopsy for a variety of reasons with no subsequent detection of the organ diseases. The FGFR1 expression was found in 98% of cases in the cells of the primary renal tumor and in 82.5% of cases in the cells of RCC metastases. In all cases, the staining intensity during the immunohistochemistry analysis was high (3+), which indicates strong expression of the receptor. Nuclear staining was obtained in 68% cases. The FGFR1 expression in cells of healthy renal tissue was found in 1 case (2.5%) due to vascular staining. Thus, this study confirmed the hypothesis of the appearance and high expression of FGFR1 in both primary tumor cells and RCC metastases (I. Tsimafeyeu et al. ESMO-ECCO 09, 2009). In subsequent studies, the concentration of FGF 1 and 2 was determined, that were the main factors with mitogenic activity in binding to FGFR1 in the plasma of 38 patients with metastatic RCC before the start of targeted therapy, with progression of the disease during the targeted therapy, and in plasma of 38 healthy volunteers (by the ELISA method). It was found that levels of both FGF were significantly lower in the blood of healthy people compared to patients with metastatic RCC. The greatest differences were shown for FGF 2 ($p<0.001$). With the progression of the disease during targeted therapy (sunitinib, sorafenib), there was a significant increase in FGF 2—by more than 50% ($p<0.001$), and FGF 1—by more than 30% ($p<0.05$), compared to the baseline FGF level. With the efficacy of the targeted therapy, changes in the level of both FGFs were not reliably observed ($p=0.3$). Median plasma concentrations of FGF 2 in patients with disease progression and without it differed significantly ($p<0.001$, FIG. 1). In addition, the study analyzed the target level for sunitinib/sorafenib—a vascular endothelial growth factor (VEGF). There were no statistical differences in the VRE plasma concentration in patients with RCC with disease progression during therapy and at the baseline (p=0.2), as well as there were no correlation between both FGF (p>0.1). Thus, the results of the KCRB-L01 and KCRB-L02 studies indicate that the FGF/FGFR1 pathological pathway is not only independent in the development of RCC, but it can decide on the resistance to existing targeted tumor therapy. Based on the foregoing, we have assumed that blocking the FGF/FGFR1 pathway may lead to the failure of the cancer cell proliferation, and to the inhibition of angiogenesis. FGFR1 antagonists, including human monoclonal antibodies, can be used to suppress tumor growth and its metastases. In addition, the production of conjugates of a monoclonal antibody (its fragments) to FGFR1 and contrast agents can be used in the diagnosis of malignant and other formations, which cells express FGFR1 in large numbers.

In one aspect, this invention relates to the in vivo treatment of an individual using an anti-FGFR1 antibody that inhibits the growth of cancerous tumors. Only one anti-FGFR1 antibody can be used to inhibit the growth of cancerous tumors. Alternatively, the anti-FGFR1 antibody can be used in combination with other immunogenic agents, with standard anticancer therapy or with other antibodies described below. Accordingly, in one embodiment, this invention relates to a method for inhibiting the growth of tumor cells in an individual, where the said method comprises administering a therapeutically effective amount of an anti-FGFR1 antibody or antigen-binding segment thereof to the said individual. A humanized anti-FGFR1 antibody (e.g., any of the humanized anti-human FGFR1-antibodies described herein) is a preferred antibody. Additionally or alternatively, the said antibody may be represented by a chimeric or human anti-FGFR1 antibody. Cancerous tumors usually susceptible to immunotherapy are the preferred cancerous tumors, the growth of which can be inhibited by the antibodies of the invention. Non-limiting examples of cancerous tumors preferred for treatment with the antibodies of the invention include renal cell carcinoma, lung cancer, breast cancer (e.g., breast carcinoma), ovarian cancer (e.g., ovarian carcinoma). Examples of other tumor diseases that can be treated by the methods of the invention include melanoma (e.g., malignant melanoma with metastases), prostate cancer, colon cancer, bone tumors, pancreatic cancer, skin cancer, brain tumors, chronic or acute leukemia, including acute myeloid leukemia, chronic myeloid leukemia, acute lymphoblastic leukemia, chronic lymphocytic leukemia, lymphomas (for example, Hodgkin's lymphoma and non-Hodgkin's lymphoma, lymphocytic lymphoma of the central nervous system, T-cell lymphoma), nasopharyngeal carcinoma, head and neck tumor, malignant skin melanoma or intraocular melanoma, uterine cancer, rectal cancer, anus cancer, stomach cancer, testicular cancer, uterine cancer, fallopian tube carcinoma, endometrial carcinoma, cervical carcinoma, vaginal carcinoma, vulvar carcinoma, esophageal cancer, small intestine cancer, endocrine system cancer, thyroid cancer, parathyroid cancer, adrenal cortex cancer, soft tissue sarcoma, urethral cancer, penis cancer, solid swelling In children, bladder cancer, kidney or ureter cancer, renal pelvic carcinoma, central nervous system (CNS) tumor, tumor angiogenesis, spine tumor, brainstem glioma, pituitary adenoma, Kaposi's sarcoma, epidermoid cancer, squamous cell carcinoma, cancerous tumors, induced by environmental exposure, including asbestos cancers, such as mesothelioma, and combinations of these cancers.

Anti-FGFR1-antibodies can be, but are not necessarily combined with an immunogenic agent, such as cancer cells, purified tumor antigens (including recombinant proteins, peptides and carbohydrate molecules), cells, and cells transfected with genes encoding immunostimulatory cytokines. Non-limiting examples of suitable antitumor vaccines include vaccines based on peptides, melanoma antigens, such as gp100 peptides, MAGE antigens, Trp-2, MART1 and/or tyrosinase, or tumor cell-based vaccines that have been transfected for the expression of the cytokine GM-CSF. Some human tumors, such as melanoma, were found to be immunogenic. In the meantime, it is assumed that with an increase in the threshold of T-cell activation by blockade of FGFR1, tumor responses can be activated in the host.

A number of experimental anticancer vaccination strategies were developed (refer to Rosenberg, S., Development of Cancer Vaccines, ASCO Educational Book Spring: 60-62, 2000; Logothetis, ASCO Educational Book Spring: 300-302, 2000; Khayat, ASCO Educational Book Spring: 414-428, 2000; Foon, ASCO Educational Book Spring: 730-738, 2000; см. также Restifo, & Sznol, Cancer Vaccines, Ch. 61, pp. 3023-3043 in DeVita, et al. (eds.), Cancer: Principles and Practice of Oncology, Fifth Edition, 1997). In one of these strategies, the vaccine is produced using autologous or allogenic tumor cells. These cellular vaccines are typically the most effective in transducing tumor cells for communicating them the ability to express GM-CSF. The GM-CSF was shown to be a potent activator of antigen presentation and can be used for anticancer vaccination (Dranoff et al. Proc. Natl. Acad. Sci U.S.A. 90: 3539-43, 1993).

Examination of gene expression and patterns of large-scale gene expression in various tumors made it possible to identify the so-called tumor-specific antigens (Rosenberg, Immunity 10: 281-7, 1999). In many cases, such tumor-specific antigens are differentiation antigens expressed in tumors and in the cells which these tumors originated from, for example, melanocyte-specific gp100 antigens, MAGE and Trp-2 antigens. It is important to emphasize that many of these antigens, as it has already been shown, are targets of tumor-specific T-cells in the host. The blockade of FGFR1 can be performed together with a set of recombinant proteins and/or peptides expressed in the tumor to generate an immune response to these proteins. Such proteins are usually identified by the immune system as autoantigens, and therefore they are tolerant to them. The tumor antigen may also be represented by a telomerase protein, which is necessary for the synthesis of chromosomal telomeres, and which is expressed in more than 85% of human cancers and in a limited number of somatic tissues only (Kim et al. Science 266: 2011-2013, 1994) (these somatic tissues can be protected from immune attack by various methods). The tumor antigens can also be represented by "neoantigens" expressed in cancer cells under the influence of somatic mutations that modify the protein sequence or result in the formation of chimeric proteins between two unrelated sequences (i.e., bcr-abl in the Philadelphia chromosome) or an idiotype of B-cell lymphoma. Other antitumor vaccines may include proteins from viruses involved in the formation of cancerous tumors in human, such as human papillomaviruses (HPV), hepatitis viruses (HBV and HCV), and Kaposi's sarcoma-associated herpesvirus (KSHV). Other forms of tumor-specific antigens that can be used in combination with the blockade of FGFR1 include purified heat shock proteins (HSPs) isolated from the very tumor tissue. These heat shock proteins contain fragments of tumor cell proteins, and such HSPs are highly effective when delivered to antigen-presenting cells for the production of antitumor immunity (Suot & Srivastava, Science 269: 1585-1588, 1995; Tamura et al. Science 278:117-120, 1997). Dendritic cells (DCs) are effective antigen-presenting cells that can be used to stimulate antigen-specific responses. The DCs can be produced ex vivo and can be loaded with various protein and peptide antigens, as well as with extracts of tumor cells (Nestle, F. et al., 1998, Nature Medicine A: 328-332). The DCs can also be transduced by genetic methods with the aim of communicating them the ability to express tumor antigens. The DCs were also directly fused to tumor cells for immunization purposes (Kugler, A. et al., 2000, Nature Medicine 6: 332-336). Immunization with DCs used for vaccination can be successfully performed in combination with PD-1 blockade to activate stronger antitumor responses. The blockade of FGFR1 can also be combined with the standard anticancer therapy. The blockade of FGFR1 can be successfully performed in combination with chemotherapy. In these cases, the dose of the chemotherapeutic agent administered can be reduced (Mokyr, M. et al., 1998, Cancer Research 58: 5301-5304). An example of such a combination includes the combination of an anti-FGFR1 antibody with decarbazine used to treat various cancers. Another example of such a combination includes the combination of an anti-FGFR1 antibody with interleukin-2 (IL-2) used to treat various cancers. In addition to combined therapy with FGFR1 blockade and chemotherapy, there is another scientific approach based on the fact that cell death, which is the result of the cytotoxic effect of most chemotherapeutic compounds, should lead to an increase in tumor antigen levels along the antigen presentation pathway.

Another combined therapy that can produce a synergistic effect in combination with FGFR1 blockade and thus lead to cell death includes radiation therapy, surgery and antihormonal therapy. Each of these strategies allows to create a source of tumor antigen from the host. The blockade of FGFR1 can also be combined with epy inhibition of angiogenesis. Inhibition of angiogenesis results to the death of tumor cells that can direct the tumor antigen into the host antigen presentation pathway. The FGFR1-blocking antibodies can also be used in combination with bispecific antibodies that direct excitatory cells expressing Fcα or Fcγ receptors to tumor cells (refer to, for example, U.S. Pat. Nos. 5,922,845 and 5,837,243). Bispecific antibodies can be used to deliver two separate antigens. For example, bispecific antibodies against the Fc receptor/tumor antigen (e.g., Her-2/neu) were used to deliver macrophages to tumor sites. Such targeted delivery can activate tumor-specific responses more effectively. The blockade of FGFR1 should lead to an increase in the T-cell component of these responses. Alternatively, the usage of bispecific antibodies that bind to a tumor antigen and a specific surface marker of dendritic cells provides for the immediate delivery of the antigen to the DCs.

Tumor escape from immune surveillance of the host occurs through a wide range of various mechanisms. Many of these mechanisms can be eliminated by inactivating proteins that are expressed by tumors and are immunosuppressive. Such proteins, among others, include TGF-beta (Kehrl, J. et al., 1986, J. Exp. Med. 163: 1037-1050), IL-10 (Howard, M. & O'Garra, A., 1992, Immunology Today 13: 198-200) и лиганд Fas (Hahne, M. et al., 1996, Science 274: 1363-1365). Antibodies against each of these molecules can be used in combination with an anti-PD-1 antibody to suppress the action of the immunosuppressive agent and to induce favourable antitumor immune responses in the host.

Other antibodies that can activate immune responses in the host can be used in combination with anti-FGFR1-antibodies. Such antibodies are represented by molecules being on the surface of dendritic cells and activating the function of DCs and antigen presentation. The anti-CD40-antibodies can serve as an effective substitute for the activity of T-helper cells (Ridge, J. et al., 1998, Nature 393: 474-478) and can be used in combination with anti-FGFR1-antibodies. Activating antibodies against T-cell costimulatory molecules, such as CTLA-4 (for example, U.S. Pat. No. 5,810,107) OX-40 (Weinberg, A. et al., 2000, Immunol. 164: 2160-2169), 4-1BB (Melero, I. et al., 1997, Nature Medicine 3: 682-685, 1997, PD-1 (del Rio et al., 2005, Eur. J. Immunol. 35:3545-60) и ICOS (Hutloff, A. et al., 1999, Nature 397: 262-266), can also be used to increase the T-cell activity.

At present, bone marrow transplantation is used to treat various tumors of the hematopoietic system. Although the "graft vs. host disease" may develop as the medical complication, however, a positive therapeutic effect can be achieved as a result of the "graft-versus-tumor" response from the host. The blockade of FGFR1 can be used to increase the efficiency of donor-transplanted tumor-specific T-cells.

Several experimental therapy strategies have also been developed that provide for ex vivo activation, expansion of antigen-specific T-cells, and adaptive transfer of these cells to the recipient to produce an antigen-specific T-cell antitumor response (Greenberg, R. & Riddell, S., 1999, Science 285: 546-51). These methods can also be applied to activate T-cell responses to infectious agents such as CMVs. It can be assumed that ex vivo activation in the presence of anti-FGFR1-antibodies will increase the number and activity of adaptively transferred T-cells. Taking into account that FGFR1 is expressed on various tumor cells, it should be noted that human antibodies, antibody compositions and methods of the invention can be applied to treat an individual with tumors, for example, a disease characterized by the presence of tumor cells expressing FGFR1, including, for example, renal cell carcinoma, lung cancer, breast cancer (e.g., breast carcinoma), ovarian cancer (e.g., ovarian carcinoma). Examples of other tumors that can be treated by the methods of the invention include melanoma (e.g., malignant melanoma with methastases), prostate cancer, colon cancer and lung cancer, bone tumors, pancreatic cancer, skin cancer, head and neck tumors, malignant melanoma on the skin or intraocular melanoma, uterine cancer, rectal cancer, anal cancer, gastric cancer, testicular cancer, fallopian tube carcinoma, endometrial carcinoma, cervical carcinoma, vaginal carcinoma, to vulvar arthropathy, Hodgkin's lymphoma, non-Hodgkin's lymphoma, acute myeloid leukemia (ALL), chronic lymphocytic leukemia (CLL), Burkitt lymphoma, anaplastic large cell lymphoma (ALCL), multiple myeloma, T-cell skin lymphoma, nodular small cell differentiated lymphoma, lymphocytic lymphoma, peripheral T-cell lymphoma, Lennert's lymphoma, immunoblastic lymphomas, T-cell leukemia/T-cell lymphoma (ATLL), adult T cell leukemia (TALL), entroblast/centrocyte (cb/cc) follicular lymphoma, activated B-cell-like (ABC) diffuse large B-cell lymphoma (DLBCL), T-cell lymphoma similar to angioimmunoblastic lymphadenopathy (AILD), HIV-associated primary effusion lymphoma, embryonic carcinomas, undifferentiated nasopharyngeal carcinomas (e.g., Schmincke tumor), Castleman's disease, Kaposi's sarcoma, multiple myeloma, Waldenstrom's macroglobulinemia and other B-cell lymphomas, esophagus cancer, small intestine cancer, endocrine system tumors, thyroid tumors, parathyroid tumors, adrenal cortex cancer, soft tissue sarcoma, urethral cancer, penile cancer, chronic or acute leukemia, including acute myeloid leukemia, chronic myeloid leukemia, acute lymphoblastic leukemia, chronic lymphocytic leukemia, solid tumors in children, lymphocytic lymphoma, bladder cancer, kidney or ureter cancer, tumors of the renal pelvis, central nervous system (CNS) tumor, primary CNS lymphoma, glioblastoma, brain tumors, nasopharyngeal carcinoma, tumor angiogenesis, spinal cord tumor, brainstem glioma, pituitary adenoma, Kaposi's sarcoma, epidermoid cancer, squamous cell carcinoma, T-cell lymphoma, cancerous tumors, induced by environmental exposure, including asbestos cancers, and combinations of these cancers.

This invention can also be used to treat metastases of malignant tumors. Accordingly, in one embodiment, this invention relates to a method for inhibiting the growth of tumor cells in an individual, where the said method comprises administering a therapeutically effective amount of an anti-FGFR1 antibody or antigen-binding segment thereof to the individual. Such antibody is usually represented by a humanized anti-FGFR1 antibody (e.g., any humanized anti-FGFR1 antibody described herein). Additionally or alternatively, such antibody may be represented by a chimeric or human anti-FGFR1 antibody.

Vaccines

The anti-FGFR1 antibodies can be used to stimulate antigen-specific immune responses by administering an anti-FGFR1 antibody in combination with an antigen of interest (e.g., with a vaccine). Pursuant thereto, in another aspect, this invention relates to a method for enhancing an immune response to an antigen in an individual; that method comprises the administration of the following to the said individual: (i) an antigen; and (ii) an anti-FGFR1 antibody or antigen-binding segment thereof, to enhance an immune response to the said antigen in that individual. In the meantime, a humanized anti-human FGFR1 antibody (e.g., any of the humanized anti-FGFR1-antibodies described herein) is the preferred antibody. Additionally or alternatively, such a antibody may be represented by a chimeric or humanized antibody. This antigen can be represented, for example, by a tumor antigen, a viral antigen, a bacterial antigen or an antigen derived from a pathogen. Non-limiting examples of such antigens include the antigens discussed in the sections above, such as the aforesaid tumor antigens (or anticancer vaccines) or antigens derived from viruses, bacteria or other pathogens. Suitable modes of in vivo and in vitro administration of antibody compositions (e.g., humanized monoclonal antibodies, multispecific and bispecific molecules and immunoconjugates) of the invention are well known to those skilled in the art and may be independently selected by one of the ordinary skill in the art. For example, antibody compositions can be injected (e.g., intravenously or subcutaneously). Suitable doses of the molecules used depend on the age and body weight of the individual, as well as on the concentration and/or formulation of this antibody composition. As previously described, the anti-FGFR1 antibodies of the invention can be administered in combination with one or more other therapeutic agents, for example, a cytotoxic agent, a radioactive toxic agent, or an immunosuppressive agent.

An antibody can be added to the said agent (as an immunocomplex), or it can be administered separately. In the latter case (separate administration), the antibody can be administered before, during or after the agent administration, or it can be administered in combination with other known therapies, such as anticancer therapy, namely, radiotherapy. The specified therapeutic agents include, among others, antitumor agents such as doxorubicin (adriamycin), cisplatinum, bleomycin sulfate, carmustine, chlorambucil and cyclophosphamide salt of hydroxyurea, which are themselves effective only in concentrations that are toxic or sub-toxic to the patient. Cisplatin is injected at a dose of 100 mg/mL every four weeks, and adriamycin is injected intravenously at a dose of 60-75 mg/mL every 21 days. The administration of humanized anti-FGFR1 antibodies or their antigen-binding fragments of the invention in combination with chemotherapeutic agents allows to deliver two anticancer agents that act by different mechanisms and have a cytotoxic effect on human tumor cells. Such joint administration allows solving the problems associated with developing the drugs resistance, or changing the antigenicity of tumor cells, which makes them resistant to this antibody.

This invention also relates to kits containing antibody compositions of the invention (e.g., humanized antibodies, bispecific or multispecific molecules, or immunoconjugates) and instructions for their use. Such a kit may also contain at least one additional reagent or one or more additional humanized antibodies of the invention (e.g., a humanized antibody with additional activity directed to binding to the epitope on the FGFR1 antigen and different from that of the first humanized antibody). Such kits are usually labelled with instructions for using the contents of that very kit. The term "label" includes any text or printed material glued on the package or enclosed in the package of this kit, or attached to this kit in some other form.

Combined Therapy

In one embodiment, this invention relates to a method of treating a hyperproliferative (oncological) disease, comprising administering an anti-FGFR1 antibody and an anti-CTLA-4 and/or PD-1 antibody to an individual. In other embodiments, the anti-FGFR1 antibody is administered at a subtherapeutic dose, the anti-CTLA-4- and/or anti-PD-1-antibody is administered at a subtherapeutic dose, or both of these antibodies are administered at a subtherapeutic dose. In another embodiment, this invention relates to a method of inhibiting a side effect associated with the treatment of a hyperproliferative disease by an immunostimulatory agent, wherein the said method comprises administering an anti-FGFR1 antibody and a subtherapeutic dose of an anti-CTLA-4- and/or anti-PD-1-antibodies to an individual. In some embodiments, the specified individual is a human. In some embodiments, the said anti-CTLA-4-antibody is represented by a monoclonal antibody with a human sequence 10D1, and the said anti-PD-1 antibody is represented by a monoclonal antibody with a human-sequence such as 17D8, 2D3, 4H1, 5C4, and 4A11. The monoclonal antibody with human sequence 10D1 was isolated and structurally identified as described in U.S. Pat. No. 6,998,420. Monoclonal antibodies with the human sequence 17D8 2D3, 4H1, 5C4 and 4A11 were isolated and structurally identified as described in U.S. Provisional Application Ser. No. 60/679, 466. A monoclonal anti-FGFR1 antibody, a monoclonal anti-CTLA-4 antibody, and a monoclonal anti-PD-1 antibody and human antibodies of the invention can be obtained by a variety of methods including a standard method for producing monoclonal antibodies, for example, a standard method for hybridising somatic cells, described by Kohler and Milstein, 1975, Nature 256:495. Herewith any method of producing monoclonal antibodies can be used, for example, a method of viral or oncogenic transformation of B-lymphocytes. A mouse is one of the animals used to obtain hybridomas. The production of hybridomas in mice is a very well-developed procedure. Protocols and immunization methods for the immunized splenocyte isolation performed for their subsequent fusion are known to those skilled in the art. Fusion partners (e.g., murine myeloma cells) and fusion procedures are also known to those skilled in the art (refer to, for example, Harlow and Lane, 1988, Antibodies, A Laboratory Manual, Cold Spring Harbor Laboratory Press, Cold Spring Harbor New York).

The combination of antibodies can be used to improve the immune response in order to suppress the hyperproliferative disease by blocking FGFR1 and PD-1 and/or CTLA-4. For example, these molecules can be injected in cell cultures, either in vitro or ex vivo, or a human, for example, in vivo, in order to improve the immune response in various situations. Pursuant thereto, in one aspect, this invention relates to a method for modifying an immune response in an individual comprising the administration of a combination of antibodies or a combination of their antigen-binding segments of the invention to the individual in order to modify the individual's immune response. In this case, it is preferable for that response to be improved, stimulated or activated. In another embodiment, this invention relates to a method of elimination of side effects associated with the treatment of a hyperproliferative disease by an immunostimulatory therapeutic agent, wherein the said method comprises the administration of an anti-FGFR1 antibody and a subtherapeutic dose of an anti-CTLA-4 antibody or anti-PD-1 antibody to an individual. Blocking of FGFR1, PD-1 and CTLA-4 with antibodies can improve the patient's immune response against cancerous cells. Malignant tumors usually susceptible to immunotherapy are the malignant tumors, the growth of which can be inhibited by the antibodies of the invention. Representative examples of malignant tumors which treatment may involve the combined therapy of the invention include renal cell carcinoma (RCC), lung cancer, melanoma (e.g., malignant melanoma with methastases), prostate cancer, breast cancer, colon cancer, lung cancer and other malignant tumors, including malignant tumors, induced by environmental exposure, including asbestos cancers, and combinations of the said malignant tumors.

This invention can also be used to treat metastases of malignant tumors. In some embodiments, the combination of therapeutic antibodies discussed herein can be administered as a single composition in a pharmaceutically acceptable carrier simultaneously, or as separate compositions of each antibody in a pharmaceutically acceptable carrier simultaneously. In another embodiment, such a combination of therapeutic antibodies can be administered sequentially. For example, an anti-FGFR1 antibody and an anti-PD-1 antibody can be administered sequentially, for example, an anti-FGFR1 antibody can be administered first, followed by an anti-PD-1 antibody, or an anti-PD-1 antibody can be administered first, followed by an anti-FGFR1 antibody. In addition, in the case of the sequential administration of more than one dose of a combination of therapeutic agents, the order of such administration may be reversed or the same for each time of administration, wherein the sequential administration can be combined with simultaneous administration, or it may be performed in any other combination. Thus, for example, the first administration can be performed by the simultaneous administration of an anti-FGFR1 antibody and an anti-PD-1 antibody in combination with each other, the second administration may include the administration of an anti-FGFR1 antibody, followed by the administration of an anti-PD-1 antibody, and during the third administration, an anti-PD-1 antibody can be administered first, followed by an anti-FGFR1 antibody, etc. Another representative scheme may include a first administration in which an anti-PD-1 antibody is administred first, followed by an anti-FGFR1 antibody, and during the second and subsequent administrations, these antibodies are administered simultaneously.

Blocking of all FGFR1 and PD-1 and/or CTLA-4 should result in an increase in the T-cell component of tumor-specific responses.

Alternatively, the usage of bispecific antibodies that bind to a tumor antigen and a specific surface marker of dendritic cells provides for the immediate delivery of the antigen to the DCs.

In another example, the antibodies of the invention can be used in combination with antitumor antibodies such as Rituxan® (rituximab), Herceptin® (trastuzumab), Bexxar® (tositumomab), Zevalin® (ibritomab), Campath® (alemtuzumab), Lymphocide® (epratuzumab), Avastin® (bevacizumab), and Tarceva® (erlotinib), etc.

In some embodiments, this invention relates to a method of elimination of side effects associated with the treatment of a hyperproliferative disease by an immunostimulatory agent, wherein the said method comprises the administration of an anti-FGFR1 antibody and a subtherapeutic dose of an anti-CTLA-4 antibody to an individual. For example, this invention relates to a method for reducing the incidence of colitis or diarrhea induced by an immunostimulatory therapeutic antibody, wherein the method comprises the administration of a nonabsorbed steroid to a patient. Since any patient treated with an immunostimulatory therapeutic antibody has a risk of developing colitis or diarrhea induced by the administration of such an antibody, this means that therapy using the methods of the invention can be effective for the entire population. Although steroids have been indicated to treat inflammatory bowel disease (IBD) and to prevent complications in IBD, they have not been used to prevent the development of IBD (to reduce the incidence of IBD) in patients who have not previously been diagnosed with IBD. Serious side effects associated with the administration of steroids, and even with the administration of nonabsorbed steroids, do not allow thier preventive use.

In other embodiments, the blocking of all FGFR1 and PD-1 and/or CTLA-4 (i.e., the use of immunostimulatory therapeutic antibodies against FGFR1 and PD-1 and/or CTLA-4) can also be combined using any nonabsorbed steroids. The term "nonabsorbable steroid" as used herein means a glucocorticoid that undergoes an intensive first pathway of metabolism first, i.e., after being metabolised in the liver, the bioavailability of such a steroid becomes low, i.e., less than about 20%. In one embodiment, the nonabsorbed steroid is represented by budesonide. Budesonide is a topical glucocorticosteroid, which is intensively metabolised after the oral administration, mainly in the liver.

ENTOCORT EC® (Astra-Zeneca) is an oral formulation of budesonide, which activity depends on pH and time of administration, and which has been developed to optimize drug delivery to the ileum and through the large intestine. ENTOCORT EC® was approved in the USA for the treatment of mild-to-moderate Crohn's disease affecting the ileum and/or the ascending colon. The oral dose of ENTOCORT EC® for the treamtent of Crohn's disease is usually 6-9 mg/day. ENTOCORT EC® is released into the small intestine, and then is absorbed and remains in the intestinal mucosa. After passing through the necessary tissue of the intestinal mucosa, ENTOCORT EC® is intensively metabolised being affected by the cytochrome P450 system in the liver, which results in the formation of metabolites with insignificant glucocorticoid activity. Therefore, its biological availability is low (about 10%).

Low bioavailability of budesonide provides for a better therapeutic index compared with other glucocorticoids with the less intense first stage of metabolism. Budesonide has fewer adverse events, including a lower suppression of hypothalamic-pituitary function, rather than systemic corticosteroids. However, the continued administration of ENTOCORT EC® can result into the development of systemic glucocorticoid effects, such as hypercorticoidism and suppression of adrenal function. Refer to PDR 58th ed. 2004; 608-610.

In other embodiments, blocking the combination of FGFR1 and PD-1 and/or CTLA-4 (i.e., by immunostimulatory therapeutic anti-FGFR1 antibody and anti-PD-1 antibody and/or anti-CTLA-4 antibody) in combination with a nonabsorbable steroid, can also be performed in combination with salicylate. Salicylates are 5-ASA compounds, such as, for example: sulfasalazine (AZULFIDINE®, Pharmacia & UpJohn); olsalazine (DIPENTUM®, Pharmacia & UpJohn); balsalazide (COLAZAL®, Salix Pharmaceuticals, Inc.) and mesalamine (ASACOL®, Procter & Gamble Pharmaceuticals; PENTASA®, Shire US; CANASA®, Axcan Scandipharm, Inc.; ROWASA®, Solvay).

In the methods of the invention, administration of salicylate in combination with an anti-FGFR1 antibody and an anti-PD-1 antibody and/or an anti-CTLA-4 antibody and a nonabsorbed steroid can be performed by almost simultaneous or sequential administration of salicylate and a nonabsorbed steroid in order to reduce the incidence of colitis induced by immunostimulating antibodies. For example, in accordance with this invention, methods for reducing the incidence of colitis induced by immunostimulatory antibodies comprise the simultaneous or sequential administration of salicylate and a nonabsorbed steroid (e.g., salicylate is administered in 6 hours after the administration of a nonabsorbed steroid), or administration thereof in any other sequence. In addition, according to this invention, salicylate and a nonabsorbed steroid can be administered in the same mode (for example, they can both be administered orally) or in various modes (e.g., salicylate is administered orally and a nonabsorbed steroid is administered rectally) that can differ from the mode(s) of administration of the anti-FGFR1 antibody, anti-PD-1 antibody and anti-CTLA-4 antibody.

Compositions of the invention (e.g., human antibodies, multispecific and bispecific molecules, and immunoconjugates) with complement-binding sites, such as parts derived from IgG1, IgG2 or IgG3 or IgM that bind to complement, can also be used in the presence of a complement. In one embodiment of the invention, ex vivo treatment of a cell population containing target cells with a binding agent of the invention and the corresponding excitatory cells, can be performed together with the administration of a complement or a complement-containing serum. The phagocytosis of target cells coated with a binding agent of the invention can be enhanced by binding to complement proteins. In another embodiment, target cells coated with specified compositions of the invention (e.g., human antibodies, multispecific and bispecific molecules) can also be lysed when exposed to a complement. In yet another embodiment, the said compositions of the invention do not activate the complement. The compositions of the invention (e.g., human antibodies, multispecific and bispecific molecules, and immunoconjugates) can also be administered in combination with the complement. Pursuant thereto, the scope of this invention encompasses compositions comprising human antibodies, multispecific and bispecific molecules, and serum or complement.

These compositions have the advantage that the said complement is located therein in close proximity to human antibodies, multispecific and bispecific molecules. Alternatively, human antibodies, multispecific and bispecific molecules of the invention and complement or serum can be administered separately.

Pursuant thereto, another therapeutic agent, such as a cytotoxic or radiotoxic drug, that enhances or improves the therapeutic effect of a human antibody can be additionally administered (before, during or after the administration of the human antibody of the invention) to the patients treated with the antibody compositions of the invention.

This invention will now be explained in greater detail with the reference to embodiments, there of which are represented in the examples, which are not to be construed as limiting the invention. The description of all publications, patents and published patent applications cited in this application is incorporated herein in its entirety by reference.

Example 1. Murine Monoclonal Antibody OCX-01 Against FGFR1, Derived from a Hybridoma Murine hybridoma PA255 clone 56 (Kidney Cancer Research. Bureau) was produced using the hybridoma method by G. Köhler, C. Milstein. J Nature 256, 495 (1975), and cultered in MegaCell™ Dulbecco's Modified Eagle's Medium (Sigma Aldrich) with 1 mmol/l glutamine, 10% FBS (Gibco, Invitrogen) and 50 µg/mL gentamicin (Sigma Aldrich) at of 37° C., 5% $CO_2$. The mammalian cell line CHO-S was obtained from Invitrogen and maintained in CHO-S-SFM II (Gibco, Invitrogen) at 37° C., 8% $CO_2$. The murine monoclonal antibody OCX-01, derived from the murine PA255 cell line clone 56, has the ability to binding with a high degree of affinity ($K_d$=4.6 nM) and the ability to influence the biological activity of the FGF receptor.

Example 1.1. mRNA Extraction and Reverse Transcription

All RNAs were extracted from the hybridoma cells using the Nucleospin RNA II system (Macherei Nagel GmbH & Co KG), according to the manufacturer's instructions, the cDNA was synthesized from 5 µg of the extracted RNA using the First Strand cDNA Synthesis system and the Mouse Ig-Primer Set (Novagen, Merck KGaA) according to the manufacturer's instructions.

Example 1.2. Amplification of Murine Ig Heavy and Light Chain Variable Regions, Cloning and Sequencing The murine VDJ and VJ arrangement for the variable regions of the heavy and light chains were amplified using the synthesized cDNAs, the Mouse Ig-primers Set, and NovaTaq DNA polymerase (Novagen, Merck KGaA). The PCR products were purified and cloned in the pSTBlue-1 AccepTor Vector system and using NovaTaq DNA polymerase (Novagen, Merck KGaA) according to the manufacturer's instructions. The plasmid DNA sequencing was performed by LGC Genomics GmbH.

The sequences of murine VDJ or VJ rearrangements were associated with widely available generational line sequences from the murine Ig heavy- and light-chain genes using the IMGT/V_QUEST software. Numerous VDJ or VJ arrangements with murine sequences were obtained using the ClustalW software.

Example 2. Obtaining Variants of Humanized Antibodies

The humanized versions of the monoclonal antibody PA255 clone 56, OCX-01, were generated using immunogenetic information and immunoinformatics, made available by the international ImMunoGeneTics® information system (IMGT®, http://www.imgt.org). Murine variable sequences of heavy and light chains (VH and VL, respectively) were compared to the human sequences of the generative line using the IMGT/V_QUEST and IMGT/DomainGapAlign tools. Components of murine sequences that differed from human components in the test segments were replaced, except for CDRs and key amino acids. The changes proposed were analyzed using IMGT/collier de perles and IMGT/3D Structure systems with the object of comparison with reference murine and human generative lines. Individual amino acids from the mouse antibody were used if they were considered as playing an important role in the formation of antibody specificity and affinity. Genes with specific mutations were synthesized using the GeneArt system (Invitrogen). After the DNA sequencing, the humanized variable regions were placed on the derived vectors of pCDNA3, as well as the expression vectors pHHU_HuIgG1 and pHHU_Huk containing the human IgG1-IGHG1*03 gene (GenBank database: Y14737) and the κ gene— IGKC*01 gene (GenBank database: J00241) representing the constant domains of the antibody heavy and light chains, respectively.

Initially, after the mRNA extraction from the cloned cell line, 56 hybridoma, nucleotide sequence codes for various domains of the heavy (VH) and light (VL) chains of the murine monoclonal antibody were obtained. The cDNA synthesis and amplification of the cDNA variable region by polymerase chain reaction (PCR) were performed using appropriate primer kits. The nucleotide and amino acid sequence codes for different domains of the murine antibody were then analyzed using the IMGT/V-QUEST and IMGT/DomainGapAlign tools and the closest human V and J genes.

The length of hypervariable sites for the heavy chain at the level of [9.7.9], as well as the closest human gene IGHV4-30-4*01 were detected (GenBank database: Z14238). There are 19 differences between OM-RCA-01 VH and the human IGHV4-30-4*01 gene (3, 5 and 11 in FR1, FR2 and FR3 IMGT structures, respectively). In the FR4-IMGT structure, the murine antibody VH residues T123 and L124 were replaced by L123 and V124 (FIG. 1) to obtain an identical sequence for the human IGHJ4-30-4*01.

The length of hypervariable sites for the light chain at the level of [7.3.9], as well as the closest human gene IGKV1-9*01 were detected (GenBank database: Z00013). There are 28 differences between OM-RCA-01 VL and the human IGKV1-9*01 gene (12, 6 and 10 in FR1, FR2 and FR3 IMGT structures, respectively). In the FR4-IMGT structure, the residue L124 of the murine VL antibody was replaced by V124 to obtain an identical sequence for the human IGKJ4*01.

The lengths of the hypervariable regions are limited by the location of FR-IMGT structures (Lefranc et al. 2003, 10). In order to preserve the location of the hypervariable regions, the residues of key and specific murine amino acids were considered potentially important for the preservation of the structure of the variable region, since contacts with hypervariable regions were meant to occur in a humanized form. From this perspective, a structure consisting of two humanized variable heavy chains (VH3 and VH4) and three humanized light chains (VL3, VL4 and VL5) was created to share them and produce a functional humanized monoclonal antibody (OM-RCA) with preservation of the antigen binding affinity of the parent murine antibody. A chimeric organism containing murine variable light (mVL2) and heavy (mVH2) chains combined with human constant regions of kappa and IgG1 heavy chains, respectively, was used as a control material.

The heavy and light chain expression vectors for humanized antibody variants were transfected to CHO-S cells using the FreeStyle™ MAX reagent (Invitrogen) in ratio of 1:1. $30 \times 10^6$ cells were transfected with 15 μg of each expression vector and 30 μL of the transfection reagent. Supernatants were obtained 3 days after transfection by means of centrifugation. The antibodies were purified on G-Sepharose (GE Healthcare) and analyzed using silver nitrate SDS-PAGE.

Example 2.1. Antibody-Binding Assay

To evaluate the chimeric antibody and recombinant humanized variants immunoreactivity with the FGFR1, microtiter plates (Greiner Bio One) were coated with 0.5 μg/mL of PA-269#37 recombinant FGFR1 (antigen) or commercial recombinant human FGFR1 (Sino Biologicals ref #10616-H08H) in 0.05 mol/l carbonate-bicarbonate buffer, pH 9.6. Bound antibodies were detected using the kappa light chain of a goat anti-human antibody conjugated with horseradish peroxidase (Sigma Aldrich) for humanized variants, or anti-mouse IgG (FK specific) antibody (Sigma Aldrich) for a chimeric antibody. Absorbance was determined at 450 nm (Multiskan EX, Thermo Electron Corporation).

Example 2.2. Surface Plasmon Resonance

Analysis of surface plasmon resonance was performed using the BIAcore T100 System Operation Kit (BIAcore; GE Healthcare). Recombinant human FGFR1 antigen PA-269#37 or recombinant human FGFR1(Sino Biologicals ref #10616-H08H) was immobilized on a CM5 sensor chip (series S, BIAcore; GE Healthcare) in 10 mmol/L sodium acetate pH 5. Different antibody variants were diluted in HBS-P buffer (10 mmol/L HEPES, pH 7.4, 0.15 mol/L NaCl and 0.05% surfactant P20) and passed over the sensor chip surface (25 μl/min). The sensory surface was washed with HBS-P buffer, and then regenerated using 10 mmol/L glycine-HCl (pH 2). Different antibody concentrations were tested (0, 1, 2, 4, 8, 16, 32, 24 and 32 nM). Different cyclic kinetic properties were determined, and the results were analyzed using the 1:1 (Langmuir) binding model, inclusive of the association rate constant ($K_{on}$), dissociation rate constant ($K_{off}$) and dissociation constant ($K_d$) (Biacore, GE Healthcare).

Example 2.3. Proliferation Assay

To assess the effect of novel humanized anti-FGFR1 antibody (OM-RCA-01) on FGF-mediated signaling, the human renal carcinoma Caki-1 FGFR1-expressing cells (Charles River) were placed in a 96-well microplate (Costar white, flat bottom No. 3917) in a total volume of 90 μL/well and incubated (0.5% FBS) with OM-RCA-01 at a concentration of 100, 10 and 1 μg/mL. The control wells were left untreated. The basic FGF was added at a concentration of 50 ng/mL three hours later. Additional control wells were treated with OM-RCA-01 with no FGF stimulation. The inhibition of cell growth was determined using the Cell Titer-Glo® by Promega.

Example 2.4. Xenograft Models 1 mm³ fragment of a Caki-1 tumor were injected to the Charles River's female nude mice (from 6 to 12 weeks old)

subcutaneously. Mice with detected tumors (mean size 80-120 mg) were randomly assigned to three groups receiving placebo, nonspecific IgG (1 or 10 mg/kg) or OM-RCA-01 (1 or 10 mg/kg); 10 mice per a group. Tumor sizes were measured twice a week using a sliding caliper. Animals were daily monitored for signs of toxicity and were humanely sacrificed, and the disease was deemed to have progressed if the tumor size reached 2000 mm$^3$. The identification of significant differences in tumor growth was the ultimate objective. The differences were considered statistically significant at P<0.05.

Example 2.5. Properties of Chimerical and Humanized Anti-FGFR1 Antibodies

Variants of humanized and chimeric genes were cloned to produce two different mammalian expression vectors (pH-HU_HulgG1 and pHHU_Huk) containing the human gene of the constant kappa chain IGKC*01 and the human gene of the constant heavy chain IgG1: IGHG1*03 and transfected into HEK-FS cells. The DNA codes for the entire light and heavy chain of each variant were tested using dideoxynucleotide sequencing.

Six variants of the humanized antibody and the control chimeric antibody were purified from the culture medium using chromatography on G-Sepharose. Purity and integrity were determined using the SDS-PAGE method under reduced and non-reduced conditions. Under non-reduced conditions, a large structure of approximately 150 kDa, corresponding to the untreated antibody, was found. Under reduced conditions, all antibodies formed two large structures with a molecular mass of about 50 kD (heavy chains) and 25 kDa (light chains).

The binding properties of candidates for the production of a humanized antibody were evaluated qualitatively and quantitatively using an enzyme immunoassay and surface plasmon resonance, respectively.

The chimeric antibody (mVH2/mVL2) and variants of the VH3A/L5 (OM-RCA-01) and VH4A/L5 (OM-RCA-02) antibodies could bind to the recombinant FGFR1-antigen PA-269 #37, immobilized on the surface of the plate during the enzyme immunoassay. Similar results were obtained when a commercially available recombinant FGFR1 antigen (Sino Biologucal, ref. No. 10616-H03H) for the production of antibodies by enzyme immunoassay was used.

To measure the interaction of a chimeric antibody and variants of a humanized antibody with a recombinant FGFR1 antigen quantitatively, the dissociation constant ($K_d$) and the association constant ($K_a$) were determined. The binding potential of mVH2/mVL2, VH3A/L5 (OM-RCA-01) and VH4A/L5 (OM-RCA-02) was within the low nanomolar range with the $K_d$ values of 1.95 nM, 1.59 nM and 1, 52 nM, respectively. Two humanized variants and a chimeric control antibody showed $K_d$ values similar to those of the parental murine antibody, indicating that the humanization process had no effect on the binding potential of the parental antibody.

Example 2.6. OM-RCA-01 Inhibits the Cell Line Proliferation of the Renal Cell Carcinoma (PCC) and FGFR1 Phosphorylation OM-RCA-01 was evaluated for an antiproliferative effect on human renal cell carcinoma cells with FGFR1-expression (Caki-1) in a model with FGF-mediated signals. The basic FGF increased the cell proliferation of the renal cell carcinoma Caki-1 (P=0.011). Cells were treated with elevated concentrations of OM-RCA-01 antibody in the range of 1 to 100 µg/mL. The antibody inhibited the FGF-mediated cell proliferation significantly, compared to the control material (P=0.02). No significant effect of the antibody on cell proliferation without previous FGF-stimulation (P=0.1) was found. Moreover, there were no cell proliferation without FGF stimulation or treatment. Pursuant thereto, it was concluded that the proliferation of the RCC cells with FGFR1 expression requires FGFR1 expression, as well as FGF stimulation. In addition, the findings confirm that FGF activation affects the RCC development.

No difference between the different doses of OM-RCA-01 were found (P=0.8, 0.6 for 10 and 100 µg/mL compared to 1 µg/mL). These data make it clear that a low dose of a highly selective antibody is sufficient to block FGFR1 in the FGFR-dependent system.

The enzyme immunoassay was used to monitor the concentration of phospho-FGFR1 in the Caki-1 renal cell carcinoma line after incubation with OM-RCA-01. OM-RCA-01 inhibited the activity of phospho-FGFR1 when used at 1-50 nmol/l.

Example 2.7. Efficacy in Xenograft Models of Human Tumors

The antitumor effect of OM-RCA-01 was studied in the FGFR1-dependent xenograft models of the RCC. For this purpose, we used Caki-1 cells with a high level of FGFR1 expression. The monoclonal OM-RCA-01 antibody was administered intraperitoneally twice a week in group 3 (1 mg/kg) and group 4 (10 mg/kg). During the study, no signs of average body weight loss or clinical manifestations of toxicity were observed. In groups 3 and 4, treatment with 1 and 10 mg/kg of OM-RCA-01 resulted in an average tumor size of 758.3 mm$^3$ and 763.8 mm$^3$ on day 13, respectively. This size was significantly smaller than in the placebo group (963.9 mm$^3$, P=0.006, P=0.021) (group 1), and the group taking non-specific IgG (1017 mm$^3$, P=0.003, P=0.01) (group 2). By day 21, a progressed disease with an increase of the tumor size of up to 2000 mm$^3$ was observed in 6 (60%) and 5 (50%) in the placebo and IgG groups. Tumors in three (30%) mice in group 3 and two (20%) mice in group 4 increased to 2000 mm$^3$. All tumors in groups 3 and 4 reached the target size by day 34 as compared to the placebo group (day 24) and IgG (day 23), which corresponded to 90 and 92% inhibition of the tumor growth.

Example 3. Studies of the Antitumor and Angiogenic Activity of OM-RCA-01 Antibody on Models of Renal Cell Carcinoma (RCC)

The proliferation of RCC cells (P=0.011) was noted in in vitro study in bFGF medium with no OM-RCA-01 added. The OM-RCA-01 antibody neutralized the effects of cell stimulation in full.

In vivo, in groups of mice that had no treatment or received nonspecific immunoglobulin, the aggressive growth of the tumor up to 2000 mm$^3$ was noted, after which the animals were sacrificed. The monoclonal OM-RCA-01 antibody suppressed tumor growth significantly (Table 2). No differences in the efficacy of doses of 1 mg/kg and 10 mg/kg were found (P=0.917), which seems to indicate a high inhibitory activity of the antibody, even being used in small doses.

TABLE 2

Frequency of increasing the tumor size up to 2000 mm³ by the end of week 3 in groups of mice

|  | Control (N = 10) | Immuno-globulin (N = 10) | OM-RCA-01, 1 mg/kg (N = 10) | OM-RCA-01, 10 mg/kg (N = 10) |
|---|---|---|---|---|
| Number of mice with a tumor size of 2000 mm³ | 6 | 5 | 3 | 2 |
| Frequency of increasing tumor size up to 2000 mm³ | 60% | 50% | 30% | 20% |

All the differences between OM-RCA-01 (1 mg/kg), OM-RCA-01 (10 mg/kg) and control groups P<0.05.

The early antitumor activity of OM-RCA-01 was also evaluated in the experiment. When the tumor volume was compared on the 13th day from the beginning of the experiment, significant positive differences were found between the primary control group and the OM-RCA-01 1 mg/kg (P=0.006) and OM-RCA-01 10 mg/kg P=0.021) treatment groups. Herewith, the mean tumor volume was 963.9 mm³ in the untreated control group, and 758.3 mm³ and 763.8 mm³ in the OM-RCA-01 groups (for 1 mg/kg and 10 mg/kg, respectively).

During the whole treatment period, no antibody toxicity was detected.

An experimental study of the anti-angiogenic activity of the OM-RCA-01 antibody blocking the activity of the FGFR-1 receptor was performed on the in vivo model of the Matrigel implant. Bevacizumab, a humanized monoclonal anti-VEGF antibody, was used as a reference sample.

It was found that, when administered three times at a dose of 10 mg/kg, OM-RCA-01 blocks angiogenesis stimulated by bFGF, not VEGF, statistically significantly. In the same regimen, bevacizumab was effective against VEGF-stimulated angiogenesis, but not when using bFGF.

In in vitro and in vivo studies, OM-RCA-01 has been shown to be a monoclonal antibody with pronounced therapeutic activity against renal cell carcinoma. The antitumor efficacy of the antibody is noted on the 13th day of treatment already.

Example 4. Studies of the Antitumor and Angiogenic Activity of OM-RCA-01 Antibody on Models of Different Tumors The following cell lines were used in the work: A549 (lung cancer, ATCC # CCL-185), HS578T (breast cancer, ATCC # HTB-126), T47D (breast cancer, ATCC # HTB-1336), in-house metastatic melanoma cell line Mel-Kor (Russian patent No. 2287578) and SVEC-4-10 (endothelial cells, ATCC # CRL-2181).

The cells were cultured in RPMI-1640 medium (PAN-ECO) (A549, HS578T, T47D, Mel-Kor) or DMEM (PAN-ECO) (SVEC-4-10) containing 10% fetal bovine serum (FCS, HyClone), 2 mM glutamine (PANECO), antibiotics (100 IU/mL of penicillin and 100 mg/mL of streptomycin (all PANECO)) at 37° C., 5% $CO_2$.

For the experiments, cells were used at a 70-80% monolayer.

Evaluation of Antibody Cytotoxicity

Cytotoxicity was evaluated in accordance with the Russian National Standard COST R ISO 10993-5-2009.

Cells ($5-10\times10^3$) were inoculated into 96-well plates (Costar, USA) in complete medium. The next day, different concentrations of the test samples, prepared by dilution with the culture medium, or the appropriate solvent (control), were inoculated into the wells. The volume of the substances inoculated was not more than 5% of the medium volume in the wells. Each concentration of the test samples was studied in triplets. The cells were incubated with the samples for 72 hours. At the end of the incubation, 20 μL tetrazolium salt MTT was added to the wells for 4 hours. Cell viability was evaluated by the colour reaction, which develops upon the repairer of tetrazolium in formazan by mitochondrial dehydrogenases. The optical density was evaluated on a spectrophotometer at excitation wavelength 540 nm. The optical density in the wells with each concentration of the test drugs was averaged, and the percentage of surviving cells at a given concentration of the test drug was calculated.

The percentage of living cells was calculated taken by the formula:

$$o = \frac{[N_1 - n] \times 100\%}{N_2}$$

$N_0$—percentage of living cells;
$N_1$—average optical density of the wells containing the cells and the test substance;
$N_2$—average optical density of the wells containing the cells only;
n—optical density of the wells containing the test substance only.

For each drug, a dose-response curve was plotted and $IC_{50}$ was determined.

The sample concentration, from which the percentage of surviving cells was less than 50% ($IC_{50}$), was calculated in the GraphPad Prizm 5 program.

The experiments were repeated at least 3 times, in three replicates per an experiment.

Anti-Proliferation Assay

The cells were cultured in triplicate in low density (30 t cells/mL) in triplets in medium of a 96-well plate containing 0.1-0.5% FCS serum. The next day, the test substance was added to the wells at the required concentrations, and 6 hours later—the fibroblast growth factor (100 ng/mL bFGF (BD Bioscience)) was added. The medium, antibiotics and drugs were changed every 3 days. Cell growth was determined using a modified Crystal violet mitogenic assay on the 7th day of the experiment. The cells were washed with PBS, fixed with 1% parafarmaldehyde on PBS and stained with a 0.5% Crystal Violet solution (Sigma Chemical Co) on ethanol. The stain was dissolved in ethanol and measured on a spectrophotometer at 540-560 nm.

The curve of cell proliferative activity inhibition was built on the basis of data on the dependence of the percentage of cells (Y-axis) on the concentration of the test substance in the plate well (X-axis). The sample concentration, from which the percentage of surviving cells was less than 50% ($IC_{50}$), was calculated in the GraphPad Prizm 5 program.

The experiments are repeated at least 3 times, in three replicates per an experiment.

Method for Assessing the Blocking of the Cell Migratory Ability by the "Wound Healing" Method SVEC-4-10 cells ($3\times10^5$ cells/mL) were inoculated into the wells of a 24-well plate in a complete DMEM medium and incubated until a monolayer was formed. The monolayer was then damaged by scraping a part of the cells. The cells were incubated in DMEM medium containing 10% FCS, 2 mM glutamine and non-cytotoxic dose of the samples, for 24 hours. The cells in serum-free DMEM were used as a negative control. The results were evaluated as the percentage of migrating cells in the test versus the control.

The Method for Assessing the Blocking of the Vascular-Like Structure (VLS) Formation The 24-well plate was coated with Matrigel (100 µl/well, with the density of 8.4 mg/mL (BD Bioscience)) and incubated for 20-30 minutes at room temperature until its complete polymerization. SVEC-4-10 cells ($5 \times 10^5$ cells/mL) were incubated in DMEM supplemented with non-cytotoxic doses of the antibody, for 30 minutes at 37° C. The cells were then transferred to Matrigel-coated wells and incubated in the $CO_2$ incubator for 4-6 hours. The cells incubated in DMEM without antibody were used as a positive control.

The cytotoxic effect of OM-RCA-01 antibody on cultures of tumor and endothelial cells was studied. According to the results of the MTT test, the OM-RCA-01 antibody showed to be non-cytotoxic and causing no death of tumor cells at the concentrations studied (from 100 µg/mL to 1.5 µg/mL) (Table 3).

TABLE 3

Cytotoxic effect of OM-RCA-01 antibody on cultures of tumor and endothelial cells

| Cell culture | Maximum concentration | Number of living cells, M ± SD |
|---|---|---|
| A549 | 100 µg/mL | 85.3 ± 2.3 |
| HS578T | 100 µg/mL | 95.3 ± 1.5 |
| T47D | 100 µg/mL | 101.7 ± 0.7 |
| Mel Kor | 100 µg/mL | 97.6 ± 5.6 |
| SVEC-4-10 | 100 µg/mL | 91.7 ± 8.7 |

Antitumor Activity of the OM-RCA-01 Antibody

The study of the antiproliferative activity of the OM-RCA-01 antibody on the FGFR1-expressing tumor cell lines was performed: A549 (lung cancer, ATCC # CCL-185), HS578T (breast cancer, ATCC # HTB-126) and T47D (breast cancer, ATCC # HTB-1336). The metastatic melanoma Mel-Kor cell line (patent RU2287578) with an unknown FGFR1 expression was also used.

The number of cells was determined on the 6th day after incubation with the test sample in the presence of bFGF. The OM-RCA-01 antibody was shown to block the proliferation of FGFR1-expressing tumor cells in a dose-dependent manner (Table 4). The test antibody did not block the proliferative activity of the metastatic melanoma Mel Kor cell line.

TABLE 4

Antiproliferative effect of OM-RCA-01 antibody on cultures of tumor cells

| Cell culture | Blockage of proliferation ($IC_{50}$ ± SD), µg/l |
|---|---|
| A549 | 9.69 ± 2.5 |
| HS578T | 128.5 ± 68.2 |
| T47D | 58.9 ± 3.24 |
| Mel Kor | NA[1] |

[1]$IC_{50}$ was not achieved

Anti-Angiogenic Activity of the OM-RCA-01 Antibody

The anti-angiogenic activity of the OM-RCA-01 antibody was studied on the murine endothelial SVEC-4-10 cell line (endothelial cells, ATCC # CRL-2181).

Table 5 summarizes the results of blocking the angiogenic activity of cells in three different tests: on inhibition of proliferative and migratory activity, blockage of vascular-like structures (VLSs).

TABLE 5

Anti-angiogenic activity of the OM-RCA-01 antibody on the SVOC-4-10 endothelial cell culture

| Cell culture | Blockage of proliferation ($IC_{50}$ ± SD), µg/l | Blockage of migration (10 µg/mL), % | Blockage of the VLS formation (10 µg/mL), % |
|---|---|---|---|
| OM-RCA-01 | 1.82 ± 0.16 | 71.7 ± 8.4 | 71.3 ± 6.9 |
| Bevacizumab | NA[1] | 64.3 ± 3.9 | 85.6 ± 11.5 |

[1]$IC_{50}$ was not achieved

The OM-RCA-01 antibody has shown to block angiogenic activity at concentrations comparable to Bevacizumab.

Migration activity was studied in the "wound healing" test. 0.1% FCS was used as the negative control (the point of maximum migration inhibition, zero point), 10% FCS was used as the positive (the point of maximum migration activity, 100%). The test antibodies (100, 50 and 10 µg/mL) were added to the SVEC-4-10 cells in DMEM containing 10% FCS. The ability of antibodies to block cell migration was evaluated 24 hours after the addition of the test samples. The OM-RCA-01 antibodies and Bevacizumab have shown to block the migration activity of endothelial cells at comparable concentrations.

Being incubated on Matrigel, endothelial cells form the primary vascular network—vascular-like structures. When the OM-RCA-01 antibodies and Bevacizumab (10 µg/mL) were added, almost complete inhibition of the formation of these structures was observed.

An in vitro experimental study of the antitumor and anti-angiogenic activity of the OM-RCA-01 antibody blocking the activity of the FGFR1 receptor on cultures of tumor and endothelial cells has been performed. Bevacizumab, a humanized monoclonal anti-VEGF antibody, was used as a reference sample.

The OM-RCA-01 was found to block the in vitro proliferative activity of cultures of tumor and endothelial cells in a dose-dependent manner. The OM-RCA-01 antibody also blocks the endothelial cell migration and the vascular-like structure formation. The anti-angiogenic activity profile of the OM-RCA-01 antibody corresponds to the profile of Bevacizumab.

The data obtained indicate that OM-RCA-01 is an advanced antitumor and anti-angiogenic substance. The findings suggest that the OM-RCA-01 antibody can block the tumor growth by two independent mechanisms: by blocking the tumor cell proliferation and inhibiting angiogenesis in tumor tissues.

Example 5. Production of Stable Cell Lines Producing Anti-FGFR1 Antibody 5.1 Production of a cDNA Encoding an Anti-FGFR1 Antibody The nucleotide sequences of the cDNA genes encoding the heavy and light chains of the OM-RCA-01 antibody (OM-1-HC and OM-1-LC, respectively) were obtained by means of chemical and enzymatic synthesis at GenScript (USA). The OM-1-HC gene contained 1418 bp, the OM-1-

LC gene contained 735 bp. After the synthesis completion, the sequences were checked by sequencing at the same company.

The recombinant plasmid DNA pCBp2-OM1s contains the following sequences: two copies of the promoter and the enhancer region of the immediate early human cytomegalovirus genes, two copies of the chimeric intron, two copies of the polyadenylation signal of the SV40 late genes, synthetic genes encoding the heavy and light chains of the OM-RCA-01 antibody, the minimal SV40 replication initiation site. The following are used as selective markers: the beta-lactamase (AmpR) gene, which provides ampicillin resistance in e. coli cells, and the blasticidin S deaminase (bsr) gene, which provides resistance to blisteridin in eukaryotes.

Plasmid pCBp2-OM1s is characterized by the following parameters:
- consists of 8028 bp,
- is 4.95 MDa,
- encodes the heavy and light chains of monoclonal OM-RCA-01 antibody,
- provides the stability of the bacterial cells, transformed by this plasmid, to ampicillin, and mammalian cells, transfected with the said plasmid, to blasticidin,
- contains unique recognition sites for the following restriction endonucleases: NheI (1125 bp), MluI (1854 bp), XbaI (3288 bp), NotI (4698 bp).

The production of plasmid pCBp2-OM1s was performed in several cloning stages.

In the first stage, the commercial plasmid pCl-neo (Promega, USA) was used, from which the plasmid pCB was obtained by inserting a second expression cassette into the 3'-flanking region of this expression cassette. Both expression cassettes had the promoter and the enhancer regions of the immediate early genes of human cytomegalovirus; chimeric introns; polyadenylation signals of the late SV40 genes obtained from the plasmid pCl-neo. The first cassette contained the recognition sites of the NheI and MluI restriction enzymes, the second cassette—of the XbaI and NotI restriction enzymes.

In the second cloning stage, the gene encoding the selective antibiotic neomycin (Neo) resistance marker was replaced by the blasticidin S deaminase (bsr) gene, which determines resistance to the antibiotic blasticidin. For this purpose, an optimized nucleotide sequence encoding the blasticidin S deaminase containing the recognition sites of the AvrII and BstBI restriction enzymes was synthesized at GenScript (USA). The synthesized gene was inserted into the plasmid pCB at the sites of the said restriction enzymes in place of the Neo gene to obtain plasmid pCBp2.

The synthesized OM-1-HC and OM-1-LC genes, encoding the heavy and light chains of the antibody, respectively, contained the recognition sites of the NheI and MluI (for OM-1-HC) and XbaI and NotI (for OM-1-LC) restriction enzymes at their ends. The OM-1-HC gene was inserted into the plasmid pCBp2 at the NheI and MluI sites to obtain plasmid pCBp2-HC, and the OM-1-LC gene was also inserted into the plasmid pCBp2 at the XbaI and NotI sites to obtain plasmid pCBp2-LC.

The plasmids pCBp2-HC and pCBp2-LC were treated with the MluI and NotI restriction enzymes and ligated to each other to obtain the resulting plasmid pCBp2-OM1s. The OM-1-HC and OM-1-LC gene sequence in this plasmid was checked by sequencing with the following primers:

```
Primers for the OM1-LC gene sequencing:
OM1-LC-F1:
CAGAAGCCAGGGAAAGCAC

OM1-LC-R1:
TGTGCCTGACTTCAGCTGTT

Primers for the OM1-HC gene sequencing:
OM1-HC-F1:
CCCTCCAGCTCTCTGGGTAC

OM1-HC-R1:
CCCAGCAGTTCTGGTGCA
```

5.2 CHO-ks1 Cell Transfection with Plasmid pCBp2-OM1s

The cells were transfected using an Electroporator (BTX Harvard Apparatus, Holliston, Mass.). 20 million cells were transferred to a 50 mL Falkon tube and centrifuged at 1000 rpm for 5 minutes. The medium was removed and the cells were redissolved in 100-800 µL of electroporation solution (BT-Express, Cat. No. 45-8050, Lot No. BT1201626) mixed with the vector DNA. The cells were transferred into an electroporatory cuvette, and an impulse was applied. Immediately after the impulse, the cells were transferred into a T150 cell culture flask containing 27 mL of growth medium. The transfection was performed two more times (total of 60 million cells) and the cells were collected in one T150 flask. All procedures were performed under sterile conditions. The cells in the T150 flask were incubated for 2 days.

Selection by Blasticidin and the stable pool generation.
Cell density: $2.26 \times 10^6$ cells/mL
Cell viability: 85.2%
Average cell diameter: 14.2 µm
Total number of living cells=67 million
This result shows that the cells retain high viability after being trasfected.

- Cells were cleaned from the T150 flask and transferred to a 50 mL Falkon tube.
- Cells were centrifuged, and the medium was separated from the cells.
- Cells were redissolved in 30 mL CDM4CHO medium supplemented with 400 µg/mL G-418 and 10 µg/mL blasticidin (Invitrogen, Cat. No. A11139-03, Lot No. 1145016).
- Cells were transferred to three CultiFlask flasks (10 mL of cell suspension in each) and mixed with 20 mL (per flask) of supplemental medium.
- Cells were incubated in a CO2 incubator on a shaker (VWR Advanced Digital Shaker) at 179 rpm.
- Cells of stable OM1 pool were then sorted by MoFLo FACS.

Cloning of single cells in 96-well plates, and enzyme immunoassay

- Feeding of OM1-7 cells (50 wells) with 100 µL of medium:
- 1:1 mixture of ExCellCHO and PowerCHO-2 with 400 µg/mL G-418 and 10 µg/mL blasticidin
- This will result in the gain of 50% of the initial concentration of antibiotics.
- Based on the ELISA results, 24 most expressed clones were selected, they were replicated in 24-well plates in 1 mL medium per well.
- Of the 24 pre-selected clones, three showed the greatest stability and productivity.

The CHO-OM8-21 cell line obtained as said above has a high productivity of 0.8 g/L OM-RCA-01 antibody, and a high antibody affinity to the FGFR1 receptor of $9.27 \times 10^{-9}$ M.

The CHO-OM8-21 cell line, registration number VKPM H-134, was deposited in the Russian National Collection of Industrial Microorganisms of the State Research Institute of Genetics and Selection of Industrial Microorganisms ("Genetika") as of Nov. 6, 2012.

The CHO-OM8-21 cell line originated from the stable anouploid CHO-S cell line (Invitrogen, Cat. No. R800-07) isolated as an individual subclone from the CHO K1 cell line. The tissue is represented by Chinese hamster ovaries (CHO), epithelial-like.

Morphology of the Cell Line

In phase contrast and light microscope, the culture is represented by a suspension of round cells having oval nuclei and containing small endosomes. The doubling time is 20-22 hours.

Cultural properties, marker signs.

The cells were modified to grow in Power CHO 2CD media without any addition of serum, proteins, and in chemical media without any addition of animal or human components. In addition, the cells grow on traditional media with the addition of serum well.

Recommended freezing conditions.

Freeze the cells at a density of $2.0 \times 10^6$ living cells/mL. Centrifuge the cell suspension, remove the supernatant and resuspend the cell pellet in the culture medium with 7.5% DMSO. Freeze to −80° C. at a controlled rate of 1° C./min. Keep cells in cryogenic vials in liquid nitrogen.

Recommended cultivation conditions.

Cultivate cells in 0.1-1.0 L vials (medium volume—20-30% of the total volume) on the orbital shaker at 100-120 rpm in a humidified atmosphere at 5% $CO_2$. The cell passaging is performed every 2-3 days by diluting the cell suspension with fresh medium. The inoculum density is $0.2$-$0.3 \times 10^6$ cells/mL, the maximum density is $3.0 \times 10^6$ cells/mL. If necessary, centrifugation can be performed at 200×g.

Produced product: monoclonal antibody for treating cancer.

Susceptibility to viral infections: vesicular stomatitis, arboviruses.

---

The invention claimed is:

1. The antibody or its functional fragment, which specifically binds fibroblast growth factor receptor 1, wherein the antibody comprises a heavy chain comprising
H-CDR1 with a SEQ ID NO:1 sequence,
H-CDR2 with a SEQ ID NO:2 sequence,
and H-CDR3 with a SEQ ID NO:3,
and light chain comprising
L-CDR1 with a SEQ ID NO:4 sequence,
L-CDR2 with a SEQ ID NO:5 sequence,
and L-CDR3 with a SEQ ID NO:6.

2. The antibody or its functional fragment according to claim 1, wherein said antibody or its functional fragment specifically binds to II and IIIc domains of the fibroblast growth factor receptor 1.

3. The antibody or its functional fragment according to claim 1, binding the fibroblast growth factor receptor 1 with a dissociation constant from $K_d$ of $2\times10^{-9}$ M to $K_d$ of $1.59\times10^{-9}$ M.

4. The antibody or its functional fragment according to claim 1, wherein it has at least one of the following characteristics:
its heavy chain comprises a variable domain with a sequence homologous to at least 90% of SEQ ID NO:7;
its light chain comprises a variable domain with a sequence homologous to at least 90% of SEQ ID NO:8;
its heavy chain has a sequence homologous to at least 90% of SEQ ID NO:9;
its light chain has a sequence homologous to at least 90% of SEQ ID NO:10.

5. The antibody or its functional fragment according to claim 1, wherein said antibody has at least one of the following characteristics:
said antibody is monoclonal;
said antibody is chimeric, humanized or human;
said antibody is of the IgA, IgD, IgE, IgG1, IgG2, IgG3, IgG4, or IgM antibody isotype;
said antibody is conjugated to a cytotoxic agent.

6. The antibody or its functional fragment according to claim 1, wherein it has at least one of the following characteristics:
its heavy chain comprises a variable domain with the SEQ ID NO:7 sequence;
its light chain comprises a variable domain with the SEQ ID NO:8 sequence;
its heavy chain has the SEQ ID NO:9 sequence;
its light chain has the SEQ ID NO:10 sequence.

7. A nucleic acid encoding the antibody or its functional fragment according to claim 1, wherein said nucleic acid has at least one of the following characteristics:
it has a sequence homologous to at least 90% of SEQ ID NO:11;
it has a sequence homologous to at least 90% of SEQ ID NO:12.

8. A nucleic acid encoding the antibody or its functional fragment according to claim 1, wherein said nucleic acid has at least one of the following characteristics:
it has the SEQ ID NO:11 sequence;
it has the SEQ ID NO:12 sequence.

9. A Chinese hamster ovary cell line comprising a nucleic acid encoding the antibody or its functional fragment according to claim 1, wherein said nucleic acid has at least one of the following characteristics:
it has a sequence homologous to at least 90% of SEQ ID NO:11;
it has a sequence homologous to at least 90% of SEQ ID NO:12;
for the production of the antibody or its functional fragment according to claim 1.

10. The Chinese hamster ovary cell according to claim 9, wherein said nucleic acid has at least one of the following characteristics:
it has the SEQ ID NO:11 sequence;
it has the SEQ ID NO:12 sequence.

11. The Chinese hamster ovary cell according to claim 9, wherein the cell line deposited in the Russian National Collection of Industrial Microorganisms under the registration number VKPM H-134.

12. A method for producing the antibody or its functional fragment according to claim 1, comprising culturing a cell line comprising a nucleic acid encoding the antibody or its functional fragment according to claim 1, wherein said nucleic acid has at least one of the following characteristics:
it has a sequence homologous to at least 90% of SEQ ID NO:11;
it has a sequence homologous to at least 90% of SEQ ID NO:12;

for the production of the antibody or its functional fragment according to claim 1 in the growth medium and isolating the antibody or its functional fragment from the aforesaid cells and/or the aforesaid medium.

13. The method according to claim 12, wherein said nucleic acid has at least one of the following characteristics:
  it has the SEQ ID NO:11 sequence;
  it has the SEQ ID NO:12 sequence.

14. The method according to claim 12, wherein the cell line deposited in the Russian National Collection of Industrial Microorganisms under the registration number VKPM H-134.

15. A pharmaceutical composition for treating an oncological disease, comprising the antibody or its functional fragment according to claim 1 in an effective quantity, and a pharmaceutically acceptable carrier.

16. The pharmaceutical composition according to claim 15 wherein the oncological disease is a renal cell carcinoma.

17. A method of treating an oncological disease, including the administration of an effective quantity of the antibody or its functional fragment according to claim 1 or a pharmaceutical composition thereof.

\* \* \* \* \*

SEQUENCE LISTING

```
<160> NUMBER OF SEQ ID NOS: 12

<210> SEQ ID NO 1
<211> LENGTH: 9
<212> TYPE: PRT
<213> ORGANISM: Mus musculus

<400> SEQUENCE: 1

Gly Tyr Ser Ile Thr Ser Asp Tyr Ala
1               5

<210> SEQ ID NO 2
<211> LENGTH: 7
<212> TYPE: PRT
<213> ORGANISM: Mus musculus

<400> SEQUENCE: 2

Ile Thr Tyr Ser Gly Thr Thr
1               5

<210> SEQ ID NO 3
<211> LENGTH: 9
<212> TYPE: PRT
<213> ORGANISM: Mus musculus

<400> SEQUENCE: 3

Ala Arg Asp Gly Asn Tyr Phe Asp Tyr
1               5

<210> SEQ ID NO 4
<211> LENGTH: 7
<212> TYPE: PRT
<213> ORGANISM: Mus musculus

<400> SEQUENCE: 4

Ser Ser Val Ser Ser Ser Tyr
1               5

<210> SEQ ID NO 5
<211> LENGTH: 3
<212> TYPE: PRT
<213> ORGANISM: Mus musculus

<400> SEQUENCE: 5
```

Arg Thr Ser
1

<210> SEQ ID NO 6
<211> LENGTH: 9
<212> TYPE: PRT
<213> ORGANISM: Mus musculus

<400> SEQUENCE: 6

Gln Gln Trp Ser Gly Tyr Pro Leu Thr
1               5

<210> SEQ ID NO 7
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Variable domain of the humanized antibody heavy
      chain

<400> SEQUENCE: 7

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Ser Trp Ile Arg Gln His Pro Gly Lys Gly Leu Glu Trp
        35                  40                  45

Ile Gly Tyr Ile Thr Tyr Ser Gly Thr Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Gly Asn Tyr Phe Asp Tyr Trp Gly Gln Gly Thr Leu Val
            100                 105                 110

Thr Val Ser Ser
        115

<210> SEQ ID NO 8
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: The variable domain of the humanized antibody
      light chain

<400> SEQUENCE: 8

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Ser Ser Ser
            20                  25                  30

Tyr Leu His Trp Tyr Gln Gln Lys Pro Gly Lys Ala Pro Lys Leu Leu
        35                  40                  45

Ile Tyr Arg Thr Ser Thr Leu Gln Ser Gly Val Pro Ser Arg Phe Ser
    50                  55                  60

```
Gly Ser Gly Ser Gly Thr Glu Phe Thr Leu Thr Ile Ser Ser Leu Gln
 65                  70                  75                  80

Pro Glu Asp Phe Ala Thr Tyr Tyr Cys Gln Gln Trp Ser Gly Tyr Pro
                 85                  90                  95

Leu Thr Phe Gly Gly Gly Thr Lys Val Glu Ile Lys
            100                 105

<210> SEQ ID NO 9
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: The humanized antibody heavy chain

<400> SEQUENCE: 9

Gln Val Gln Leu Gln Glu Ser Gly Pro Gly Leu Val Lys Pro Ser Gln
  1               5                  10                  15

Thr Leu Ser Leu Thr Cys Thr Val Ser Gly Tyr Ser Ile Thr Ser Asp
                 20                  25                  30

Tyr Ala Trp Ser Trp Ile Arg Gln His Pro Gly Lys Gly Leu Glu Trp
             35                  40                  45

Ile Gly Tyr Ile Thr Tyr Ser Gly Thr Thr Tyr Tyr Asn Pro Ser Leu
 50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Asp Gly Asn Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Arg Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
        290                 295                 300
```

```
Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Glu Glu Met Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 10
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Humanized antibody light chain

<400> SEQUENCE: 10

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Ser Ser Ser
            20                  25                  30

Tyr Leu His Trp Tyr Gln Gln Lys Pro Gly Lys Ala Pro Lys Leu Leu
        35                  40                  45

Ile Tyr Arg Thr Ser Thr Leu Gln Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Gln Gln Trp Ser Gly Tyr Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205
```

Ser Phe Asn Arg Gly Glu Cys
    210                 215

<210> SEQ ID NO 11
<211> LENGTH: 1416
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Encodes the humanized antibody heavy chain

<400> SEQUENCE: 11

```
aagcttgccg ccaccatgag agtgctgatt cttttgtggc tgttcacagc ctttcctggt      60
atcctgtctc aggtgcagct gcaggagtcg ggcccaggac tggtgaagcc ttcacagacc     120
ctgtccctca cctgcactgt ctctggctac tcaatcacca gtgattatgc ctggagctgg     180
atccgccagc acccagggaa gggcctggag tggattgggt acataaccta cagtggtacc     240
acttactaca acccgtccct caagagtcga gttaccatat cagtagacac gtctaagaac     300
cagttctccc tgaagctgag ctctgtgact gccgcggaca cggccgtgta ttactgtgca     360
agagatggta actactttga ctactggggc caaggaaccc tggtcaccgt ctcctcagcg     420
tcgaccaagg gcccatcggt cttccccctg gcaccctcct ccaagagcac ctctggggc     480
acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagagagt tgagcccaaa     720
tcttgtgaca aaactcacac atgcccaccg tgcccagcac ctgaactcct ggggggaccg     780
tcagtcttcc tcttcccccc aaaacccaag gacaccctca tgatctcccg gacccctgag     840
gtcacatgcg tggtggtgga cgtgagccac gaagaccctg aggtcaagtt caactggtac     900
gtggacggcg tggaggtgca taatgccaag acaaagccgc gggaggagca gtacaacagc     960
acgtaccgtg tggtcagcgt cctcaccgtc ctgcaccagg actggctgaa tgcaaggag    1020
tacaagtgca aggtctccaa caaagccctc ccagccccca tcgagaaaac catctccaaa    1080
gccaaagggc agccccgaga accacaggtg tacaccctgc ccccatcccg ggaggagatg    1140
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctatagc aagctcaccg tggacaagag caggtggcag    1320
caggggaacg tcttctcatg ctccgtgatg catgaggctc tgcacaacca ctacacgcag    1380
aagagcctct ccctgtcccc gggtaaataa tctaga                              1416
```

<210> SEQ ID NO 12
<211> LENGTH: 735
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Encodes the humanized antibody light chain

<400> SEQUENCE: 12

```
aagcttgccg ccaccatgga tttacaggtg cagattatca gcttcctgct aatcagtgtc      60
```

```
acagtcataa tgtccagagg agacatccag ttgacccagt ctccatcctt cctgtctgca    120
tctgtaggag acagagtcac catcacttgc cgggccagtt caagtgtaag ttccagttac    180
ttacactggt atcagcaaaa accagggaaa gcccctaagc tcctgatcta taggacatcc    240
actttgcaaa gtggggtccc atcaaggttc agcggcagtg gatctgggac agaattcact    300
ctcacaatca gcagcctgca gcctgaagat tttgcaactt attactgtca gcagtggagt    360
ggttacccat tgacgttcgg cggagggacc aaggtggaga tcaaacgaac tgtggctgca    420
ccaagtgtct tcatcttccc gccatctgat gagcagttga atctggaac tgcctctgtt     480 gtgtgcctgc tgaataactt ctatcccaga gaggccaaag tacagtggaa ggtggataac    540
gccctccaat cgggtaactc ccaggagagt gtcacagagc aggacagcaa ggacagcacc    600
tacagcctca gcagcaccct gacgctgagc aaagcagact acgagaaaca caaagtctac    660
gcctgcgaag tcacccatca gggcctgagc tcgcccgtca caaagagctt caacagggga    720
gagtgttaat ctaga                                                     735
```